United States Patent
Ames et al.

(10) Patent No.: US 12,246,041 B2
(45) Date of Patent: Mar. 11, 2025

(54) METHODS AND ARTICLES OF MANUFACTURE FOR ANIMAL THERAPEUTICS

(71) Applicant: ANICELL BIOTECH, LLC, Chandler, AZ (US)

(72) Inventors: Brandon Ames, Gilbert, AZ (US); Christopher A. Bradley, Chandler, AZ (US); Tammi Epp, Chandler, AZ (US)

(73) Assignee: ANICELL BIOTECH, LLC, Chandler, AZ (US)

( * ) Notice: Subject to any disclaimer, the term of this patent is extended or adjusted under 35 U.S.C. 154(b) by 0 days.

(21) Appl. No.: 18/196,939

(22) Filed: May 12, 2023

(65) Prior Publication Data

US 2023/0364154 A1    Nov. 16, 2023

Related U.S. Application Data

(60) Provisional application No. 63/341,363, filed on May 12, 2022.

(51) Int. Cl.
   *A61K 35/50*    (2015.01)
   *A61K 9/19*    (2006.01)
   *A61K 35/24*    (2015.01)

(52) U.S. Cl.
   CPC ............... *A61K 35/50* (2013.01); *A61K 9/19* (2013.01); *A61K 35/24* (2013.01)

(58) Field of Classification Search
   None
   See application file for complete search history.

(56) References Cited

U.S. PATENT DOCUMENTS 10,993,968 B2    5/2021  Ames et al.

OTHER PUBLICATIONS

Vornhagen et al., J. Infect. Dis. 217: 1627 (2018).*
Jay Vornhagen, et al. "Human Cervical Mucus Plugs Exhibit insufficiencies in Antimicrobial Activity Towards Group B *Streptococcus*" 1626-1636. The Journal of Infectious Diseases. JID 2018:217 (May 15). Web. May 15, 2018; p. 1627, first col. last paragraph.
S C Loux, et al. "Characterization of the cervical mucus plug in mares" 197-210. Reproduction (2017) 153. Web. 2017; p. 153, second col. fifth and sixth paragraphs.
International Search Report & Written Opinion, for Application No. PCT/US2023/022088, mailed Aug. 21, 2023.
N. Becher, et al., "The cervical mucus plug: Structured review of the literature", Acta Obstetricia et Gynecologica, 2009; vol. 88, pp. 502-513, DOI: 10.1080/00016340902852898.
Shu et al., "The Beneficial Effect of Human Amnion Mesenchymal Cells in Inhibition of Inflammation and Induction of Neuronal Repair in EAE Mice", Hindawi, Journal of Immunology Research, vol. 2018, Article ID 5083797, 11 pages, 2018, https://doi.org/10.1155/2018/5083797.

(Continued)

*Primary Examiner* — Erin M. Bowers
(74) *Attorney, Agent, or Firm* — SNELL & WILMER L.L.P.

(57) ABSTRACT

A medicament is provided including, for example, a dried particulate mixture of decellularized amniotic material and a powdered, lyophilized mixture of cervical mucus plug. The medicament may be useful in treating infectious disease, for example, viral diseases, in promoting repair of tissue and halting disease progression.

16 Claims, 12 Drawing Sheets

| (pg/ml) | CMP-1 | CMP-2 | pg/mg S/M | | |
|---|---|---|---|---|---|
| IFNg | 0.0 | 0.0 | | | |
| IL-1a | 0.0 | 0.0 | | | |
| IL-1ra | 0.0 | 0.0 | | | |
| IL-2 | 0.0 | 0.0 | | | |
| IL-4 | 0.0 | 37.7 | 27.1 | | |
| IL-8 | 0.0 | 0.0 | | | |
| IL-10 | 0.0 | 0.0 | | | |
| IL-15 | 350.1 | 0.0 | 252.0 | | |
| MCP-1 | 0.0 | 0.0 | | | |
| VEGF | 0.0 | 0.0 | | | |

(56) References Cited

OTHER PUBLICATIONS

Jafari et al., "Human amniotic mesenchymal stem cells to promote/suppress cancer: two sides of the same coin", Stem Cell Research & Therapy, 12:126 (2021), pp. 1-11, https://doi.org/10.1186/s13287-021-02196-x.

Aziz et al., "An update clinical application of amniotic fluid-derived stem cells (AFSCs) in cancer cell therapy and tissue engineering", Artificial Cells, Nanomedicine, and Biotechnology, 2017, vol. 45, No. 4, pp. 765-774, DOI: 10.1080/21691401.2016.1216857, http://dx.doi.org/10.1080/21691401.2016.1216857.

Elkhenany et al., "Applications of the amniotic membrane in tissue engineering and regeneration: the hundred-year challenge", Stem Cell Research & Therapy, (2022), 13:8, pp. 1-19, https://doi.org/10.1186/s13287-021-02684-0.

Jafari et al., "Tumor Targeting by Conditioned Medium Derived From Human Amniotic Membrane: New Insight in Breast Cancer Therapy", Technology in Cancer Research & Treatment, Sage Journals, vol. 20, 2021, pp. 1-12, https://doi.org/10.1177/15330338211036318.

Tiwari, et al., "Drug delivery systems: an updated review", International Journal of Pharmaceutical Investigation, Jan. 2012, vol. 2, Issue 1, pp. 1-10, DOI: 10.4103/2230-973X.96920.

Vargason et al., "The evolution of commercial drug delivery technologies", Nature Biomedical Engineering, vol. 5, Sep. 2021, pp. 951-967, https://doi.org/10.1038/s41551-021-00698-w.

McDonald et al, :"Immunosuppressive potential of human amnion epithelial cells in the treatment of experimental autoimmune encephalomyelitis", Journal of Neuroinflammation, (2015), 12:112, pp. 1-14, DOI: 10.1186/s12974-015-0322-8.

Wassmer and Berishvili., "Immunomodulatory Properties of Amniotic Membrane Derivatives and Their Potential in Regenerative Medicine", Current Diabetes Reports, (2020), 20: 31, pp. 1-10, https://doi.org/10.1007/s11892-020-01316-w.

Bu et al., "Human amniotic epithelial cells inhibit growth of epithelial ovarian cancer cells via TGF-β 1-mediated cell cycle arrest", International Journal of Oncology, 51: 2017, pp. 1405-1414, DOI: 10.3892/ijo.2017.4123.

Nikejad et al., "Induction of apoptosis, stimulation of cell-cycle arrest and inhibition of angiogenesis make human amnion-derived cells promising sources for cell therapy of cancer", Springer, Cell Tissue Res (2016) 363, pp. 599-608, DOI 10.1007/s00441-016-2364-3.

Bhagwat and Vaidhya, "Novel Drug Delivery Systems: an Overview", International Journal of Pharmaceutical Sciences and Research, 2013, vol. 4, Issue 3, pp. 970-982, ISSN: 0975-8232.

Kang et al., "Potential antitumor therapeutic strategies of human amniotic membrane and amniotic fluid-derived stem cells", Cancer Gene Therapy (2012) 19, pp. 517-522, doi:10.1038/cgt.2012.30.

Silini et al., "Soluble Factors of Amnion-Derived Cells in Treatment of Inflammatory and Fibrotic Pathologies", Current Stem Cell Research & Therapy, 2013, vol. 8, No. 1, 10 pages, https://www.academia.edu/12699679/Soluble_Factors_of_Amnion_Derived_Cells_in_Treatment_of_Inflammatory_and_Fibrotic_Pathologies?from=cover_page.

Tehrani et al., "A Review on Modifications of Amniotic Membrane for Biomedical Applications", Frontiers in Bioengineering and Biotechnology, Jan. 2021, vol. 8, Article 606982, pp. 1-25, https://doi.org/10.3389/fbioe.2020.606982.

Liu et al., "Characteristics and Therapeutic Potential of Human Amnion-Derived Stem Cells", International Journal of Molecular Sciences, 2021, 22, 970. pp. 1-31, https://doi.org/10.3390/ijms22020970.

* cited by examiner

| (pg/ml) | CMP-1 | CMP-2 | pg/mg S/M | |
|---|---|---|---|---|
| IFNg | 0.0 | 0.0 | | |
| IL-1a | 0.0 | 0.0 | | |
| IL-1ra | 0.0 | 0.0 | | |
| IL-2 | 0.0 | 0.0 | | |
| IL-4 | 0.0 | 37.7 | 27.1 | |
| IL-8 | 0.0 | 0.0 | | |
| IL-10 | 0.0 | 0.0 | | |
| IL-15 | 350.1 | 0.0 | 252.0 | |
| MCP-1 | 0.0 | 0.0 | | |
| VEGF | 0.0 | 0.0 | | |

FIG. 1

| (pg/mL) | SA1: 2018 AMNIO M GUANIDINE | SA2: 2018 AMNIO M GUANIDINE TCA | SA3: 2018 AMNIO M UREA | SA4: 2018 AMNIO M UREA TCA | SA5: 2021 AMNIO M GUANIDINE TCA | SA6: 2021 AMNIOTIC FLUID |
|---|---|---|---|---|---|---|
| IFNg | 0.0 | 27.9 | 0.0 | 29.1 | 46.1 | 0.0 |
| IL-1a | 0.0 | 0.0 | 0.0 | 0.0 | 5.0 | 0.8 |
| IL-1ra | 51585.6 | 8.1 | 46306.0 | 245.4 | 255.2 | 10756.4 |
| IL-2 | 0.0 | 0.0 | 0.0 | 0.0 | 0.0 | 0.0 |
| IL-4 | 0.0 | 0.0 | 0.0 | 194.8 | 0.0 | 412.0 |
| IL-8 | 54.7 | 0.0 | 30.4 | 0.0 | 0.0 | 49.4 |
| IL-10 | 0.0 | 0.1 | 0.0 | 0.9 | 0.0 | 1.6 |
| IL-15 | 0.0 | 0.0 | 0.0 | 0.0 | 0.0 | 0.0 |
| MCP-1 | 108.3 | 0.0 | 55.1 | 1.3 | 0.0 | 120.1 |
| VEGF-A | 181.9 | 0.0 | 84.1 | 0.0 | 8.2 | 9.4 |

FIG. 2A

| (pg/mL) | SA1: 2018 AMNIO M GUANIDINE | SA2: 2018 AMNIO M GUANIDINE TCA | SA3: 2018 AMNIO M UREA | SA4: 2018 AMNIO M UREA TCA | SA5: 2021 AMNIO M GUANIDINE TCA |
|---|---|---|---|---|---|
| IFNg | 0.0 | 20.1 | 0.0 | 21.0 | 33.2 |
| IL-1a | 0.0 | 0.0 | 0.0 | 0.0 | 7.2 |
| IL-1ra | 7431.3 | 5.8 | 6670.7 | 176.8 | 183.8 |
| IL-2 | 0.0 | 0.0 | 0.0 | 0.0 | 0.0 |
| IL-4 | 0.0 | 0.0 | 0.0 | 140.3 | 0.0 |
| IL-8 | 7.9 | 0.0 | 4.4 | 0.0 | 0.0 |
| IL-10 | 0.0 | 0.1 | 0.0 | 0.6 | 0.0 |
| IL-15 | 0.0 | 0.0 | 0.0 | 0.0 | 0.0 |
| MCP-1 | 15.6 | 0.0 | 7.9 | 0.9 | 0.0 |
| VEGF-A | 26.2 | 0.0 | 12.1 | 0.0 | 5.9 |

FIG. 2B

Combined Supplemental Summary Information

| MW [kDa] | Description |
|---|---|
| 19.8 | 15 kDa protein B-like [Equus caballus] |
| 42 | actin, alpha cardiac muscle 1 isoform 1 [Equus caballus] |
| 37.2 | actin, alpha cardiac muscle 1 isoform 2 [Equus caballus] |
| 42 | actin, alpha skeletal muscle isoform X2 [Equus caballus] |
| 43.7 | actin, aortic smooth muscle isoform X2 [Equus caballus] |
| 42 | actin, aortic smooth muscle isoform X3 [Equus caballus] |
| 41.8 | actin, gamma-enteric smooth muscle isoform 1 [Equus caballus] |
| 41.7 | Actin, cytoplasmic 1; AltName: Full=Beta-actin; Contains: RecName: Full=Actin, cytoplasmic 1, N-terminally processed |
| 37 | actin, cytoplasmic 2 [Equus caballus] |
| 5.2 | albumin, partial [Equus caballus] |
| 23.1 | alpha-1-acid glycoprotein 2-like [Equus caballus] |
| 27.3 | alpha-1-acid glycoprotein 2-like isoform X1 [Equus caballus] |
| 27.1 | alpha-1-acid glycoprotein 2-like isoform X2 [Equus caballus] |
| 23.3 | alpha-1-acid glycoprotein 2-like isoform X3 [Equus caballus] |
| 61 | alpha-1B-glycoprotein [Equus caballus] |
| 162.6 | alpha-2-macroglobulin-like protein 1 [Equus caballus] |
| 38.7 | Annexin A1; AltName: Full=Annexin I; AltName: Full=Annexin-1; AltName: Full=Calpactin II; AltName: Full=Calpactin-2; AltName: Full=Lipocortin I |
| 21.8 | annexin A1-like isoform X1 [Equus caballus] |
| 19.2 | annexin A1-like isoform X2 [Equus caballus] |
| 17.9 | annexin A1-like isoform X3 [Equus caballus] |
| 38.6 | annexin A2 [Equus caballus] |
| 38.6 | annexin A2-like protein [Equus caballus] |
| 15.7 | antileukoproteinase isoform X1 [Equus caballus] |
| 14 | antileukoproteinase isoform X2 [Equus caballus] |
| 21.3 | azurocidin-like [Equus caballus] |
| 38.5 | beta-2-glycoprotein 1 [Equus caballus] |
| 13.4 | beta-2-microglobulin isoform X2 [Equus caballus] |
|  | beta-actin-like protein 2 isoform X1 [Equus caballus] |
|  | beta-actin-like protein 2 isoform X2 [Equus caballus] |
| 7.4 | beta-defensin 1 [Equus caballus] |
| 23.6 | brain acid soluble protein 1 [Equus caballus] |
|  | C4b-binding protein alpha chain isoform X10 [Equus caballus] |
| 78.1 | cadherin-13 precursor [Equus caballus] |
| 16.8 | calmodulin [Equus caballus] |
| 16.9 | calmodulin 2 (phosphorylase kinase, delta) [Equus caballus] |
| 17.3 | cathelicidin-2-like [Equus caballus] |
| 170.6 | CD109 antigen [Equus caballus] |
|  | CD9 antigen [Equus caballus] |
| 269.9 | centriolin [Equus caballus] |
| 121.9 | ceruloplasmin [Equus caballus] |
| 4.5 | ceruloplasmin precursor, partial [Equus caballus] |
| 42.9 | chitinase-3-like protein 1 isoform X1 [Equus caballus] |

FIG. 7A

| MW [kDa] | Description |
|---|---|
| 42.6 | chitinase-3-like protein 1 isoform X2 [Equus caballus] |
| 51.3 | chitotriosidase [Equus caballus] |
| 49.3 | chitotriosidase-1 isoform X1 [Equus caballus] |
| 46.4 | chitotriosidase-1 isoform X2 [Equus caballus] |
| 51.4 | chitotriosidase-1 precursor [Equus caballus] |
| 45.3 | chromosome 26 open reading frame, human C3orf38 [Equus caballus] |
|  | Chromogranin-A; Short=CgA; Contains: RecName: Full=Pancreastatin; Contains: RecName: Full=WE-14; Flags: Precursor |
| 52.1 | Clusterin; Contains: RecName: Full=Clusterin beta chain; Contains: RecName: Full=Clusterin alpha chain; Flags: Precursor |
| 8.6 | complement C3 precursor, partial [Equus caballus] |
| 185.7 | complement C3-like [Equus caballus] |
| 105.1 | complement component C6 [Equus caballus] |
| 85.9 | complement factor B [Equus caballus] |
| 25.6 | Complement factor B-like protein, partial [Equus caballus] |
| 75.4 | complement factor I isoform X1 [Equus caballus] |
| 70.3 | complement factor I isoform X2 [Equus caballus] |
| 53.9 | COP9 signalosome complex subunit 1 isoform X2 [Equus caballus] |
| 53.5 | COP9 signalosome complex subunit 1 isoform X3 [Equus caballus] |
|  | corticosteroid-binding globulin isoform X1 [Equus caballus] |
|  | corticosteroid-binding globulin isoform X2 [Equus caballus] |
| 108.4 | deleted in malignant brain tumors 1 protein [Equus caballus] |
| 54.8 | EGF-containing fibulin-like extracellular matrix protein 1 isoform X2 [Equus caballus] |
| 16.1 | epididymal secretory protein E1 isoform X3 [Equus caballus] |
| 34.9 | estrogen sulfotransferase [Equus caballus] |
| 32.8 | estrogen sulfotransferase-like [Equus caballus] |
|  | ezrin [Equus caballus] |
| 63.4 | galectin-3-binding protein [Equus caballus] |
| 19.8 | ganglioside GM2 activator isoform X1 [Equus caballus] |
| 20.6 | ganglioside GM2 activator isoform X2 [Equus caballus] |
| 20.6 | ganglioside GM2 activator precursor [Equus caballus] |
|  | PREDICTED: granzyme B-like [Equus caballus] |
| 38.4 | haptoglobin [Equus caballus] |
| 14.1 | histone H2A type 1-C-like [Equus caballus] |
| 14.1 | histone H2A type 1-D-like [Equus caballus] |
| 14.1 | histone H2A type 1-E-like [Equus caballus] |
| 27.3 | histone H2A type 1-like [Equus caballus] |
| 14.1 | histone H2A type 2-A-like [Equus caballus] |
| 14.1 | histone H2A type 3-like [Equus caballus] |
| 11.4 | histone H4-like [Equus caballus] |
| 13.5 | Ig lambda chain - horse |
| 12.1 | Ig lambda chain C region - horse (fragment) |
| 57.1 | Ig mu chain C region membrane-bound form isoform X1 [Equus caballus] |
| 57 | Ig mu chain C region membrane-bound form isoform X2 [Equus caballus] |
| 56 | Ig mu chain C region membrane-bound form isoform X3 [Equus caballus] |
| 53.6 | Ig mu chain C region membrane-bound form isoform X4 [Equus caballus] |
| 49.4 | Ig mu chain C region membrane-bound form isoform X5 [Equus caballus] |

FIG. 7B

| MW [kDa] | Description |
|---|---|
| 42.7 | Ig mu chain C region membrane-bound form isoform X6 [Equus caballus] |
| 295.3 | IgGFc-binding protein [Equus caballus] |
| 23.1 | immmunoglobulin lambda light chain variable region, partial [Equus caballus] |
| 37 | immunoglobulin alpha constant heavy chain, partial [Equus caballus] |
| 46.9 | immunoglobulin G heavy chain, partial [Equus caballus] |
| 24.2 | immunoglobulin G light chain, partial [Equus caballus] |
| 37.4 | immunoglobulin gamma 1 heavy chain constant region, partial [Equus caballus] |
| 37.5 | immunoglobulin gamma 2 heavy chain constant region, partial [Equus caballus] |
| 38.7 | immunoglobulin gamma 3 heavy chain constant region, partial [Equus caballus] |
| 36.5 | immunoglobulin gamma 4 heavy chain constant region, partial [Equus caballus] |
| 35.9 | immunoglobulin gamma 5 heavy chain constant region, partial [Equus caballus] |
| 35.9 | immunoglobulin gamma 6 heavy chain constant region, partial [Equus caballus] |
| 36.5 | immunoglobulin gamma 7 heavy chain constant region, partial [Equus caballus] |
| 19.6 | immunoglobulin heavy chain V-D-J region, partial [Equus caballus] |
| 17.8 | immunoglobulin J polypeptide, linker protein for immunoglobulin alpha and mu polypeptides precursor [Equus caballus] |
| 25.2 | immunoglobulin kappa light chain [Equus caballus] |
| 19.1 | immunoglobulin kappa light chain V-J region, partial [Equus caballus] |
| 11.2 | immunoglobulin lambda light chain constant region, partial [Equus caballus] |
| | |
| 22.8 | immunoglobulin lambda light chain V-J region, partial [Equus caballus] |
| 24.6 | immunoglobulin lambda-like polypeptide 5 [Equus caballus] |
| 17.8 | immunoglobulin lambda-like polypeptide 5-like [Equus caballus] |
| 49.4 | immunoglobulin mu heavy chain constant chain secreted form, partial [Equus caballus] |
| | Inhibin beta A chain; AltName: Full=Activin beta-A chain; Flags: Precursor |
| 77.5 | inhibitor of carbonic anhydrase-like [Equus caballus] |
| 14.6 | interferon-induced transmembrane protein 3 [Equus caballus] |
| 64.7 | keratin, type II cytoskeletal 1 isoform X1 [Equus caballus] |
| 63.3 | keratin, type II cytoskeletal 2 epidermal-like [Equus caballus] |
| 77.3 | lactotransferrin precursor [Equus caballus] |
| 75.9 | Lactotransferrin; Short=Lactoferrin; Flags: Precursor |
| 23.5 | lambda-immunoglobulin [Equus caballus] |
| 39.4 | leucine zipper protein 2 isoform X1 [Equus caballus] |
| 39.1 | leucine zipper protein 2 isoform X2 [Equus caballus] |
| | L-amino-acid oxidase-like [Equus caballus] |
| 36.6 | L-lactate dehydrogenase A chain [Equus caballus] |
| 39.7 | L-lactate dehydrogenase A chain isoform X1 [Equus caballus] |
| 36.5 | L-lactate dehydrogenase B chain [Equus caballus] |
| 36.5 | L-lactate dehydrogenase B chain-like protein [Equus caballus] |
| 41.3 | L-lactate dehydrogenase C chain isoform X3 [Equus caballus] |
| 36 | L-lactate dehydrogenase C chain isoformX1 [Equus caballus] |
| | lymphocyte antigen 6H-like [Equus caballus] |
| 16.7 | lysozyme C, milk isozyme isoform 1 [Equus caballus] |
| 3.7 | Lysozyme C, spleen isozyme; AltName: Full=1,4-beta-N-acetylmuramidase C |
| 126.3 | mucin-4 [Equus caballus] |
| 486.6 | mucin-5AC [Equus caballus] |
| 182.2 | mucin-5B [Equus caballus] |

FIG. 7C

| MW [kDa] | Description |
|---|---|
| 228.8 | mucin-6 [Equus caballus] |
| 17.6 | myeloid cathelicidin 1 [Equus caballus] |
| 18.1 | myeloid cathelicidin 2 precursor [Equus caballus] |
| 19.3 | myeloid cathelicidin 3 precursor [Equus caballus] |
| 293.7 | neurobeachin-like 1 [Equus caballus] |
| 46.5 | neuroserpin isoform X3 [Equus caballus] |
| 33.9 | neutrophil gelatinase-associated lipocalin isoform X2 [Equus caballus] |
| 24.9 | neutrophil gelatinase-associated lipocalin isoform X3 [Equus caballus] |
| 24.8 | neutrophil gelatinase-associated lipocalin isoform X4 [Equus caballus] |
| 23.1 | neutrophil gelatinase-associated lipocalin isoform X6 [Equus caballus] |
| 57 | olfactomedin-4 [Equus caballus] |
| 50.6 | pantetheinase [Equus caballus] |
| 66.2 | phenylalanine--tRNA ligase beta subunit [Equus caballus] |
|  | phosphatidylethanolamine-binding protein 4 isoform X3 [Equus caballus] |
| 63.8 | phospholipase B domain containing 1 [Equus caballus] |
| 54.7 | phospholipid transfer protein isoform X2 [Equus caballus] |
|  | Plasminogen; Contains: RecName: Full=Plasmin heavy chain A; Contains: RecName: Full=Plasmin light chain B |
|  | plasminogen-like isoform 1 [Equus caballus] |
| 83 | polymeric immunoglobulin receptor [Equus caballus] |
| 83.2 | polymeric immunoglobulin receptor precursor [Equus caballus] |
| 42.8 | polyubiquitin-C [Equus caballus] |
| 58.5 | proactivator polypeptide isoform X1 [Equus caballus] |
| 58.3 | proactivator polypeptide isoform X2 [Equus caballus] |
| 58.1 | proactivator polypeptide isoform X3 [Equus caballus] |
| 50.6 | properdin [Equus caballus] |
|  | prostate stem cell antigen [Equus caballus] |
| 198.4 | proteasome activator complex subunit 4 [Equus caballus] |
| 10.5 | protein S100-A12 [Equus caballus] |
| 10.4 | protein S100-A8 [Equus caballus] |
| 19 | protein S100-A9 isoform X1 [Equus caballus] |
| 17.4 | protein S100-A9 isoform X2 [Equus caballus] |
| 17.4 | protein S100-A9-like [Equus caballus] |
| 36.5 | ras-related GTP-binding protein A [Equus caballus] |
| 21.3 | Ras-related GTP-binding protein A-like protein, partial [Equus caballus] |
| 41 | ras-related GTP-binding protein B [Equus caballus] |
|  | ras-related protein Rap-1A isoform X2 [Equus caballus] |
|  | ras-related protein Rap-1b [Equus caballus] |
| 22.5 | resistin [Equus caballus] |
| 30.6 | retinoic acid receptor responder protein 1 [Equus caballus] |
|  | Retinol-binding protein 4; AltName: Full=Plasma retinol-binding protein; Short=PRBP; Short=RBP; Flags: Precursor |
|  | ribonuclease T2 [Equus caballus] |
| 9.7 | secretoglobin family 1A member 1 variant B-like protein [Equus caballus] |
| 9.6 | secretoglobin family 1A member 1P variant A-like protein [Equus caballus] |
|  | secretoglobin, partial [Equus caballus] |
| 48.8 | serine peptidase inhibitor clade A (alpha-1 antiproteinase, antitrypsin) member 14 |

FIG. 7D

| MW [kDa] | Description |
|---|---|
| | precursor [Equus caballus] |
| | serine protease inhibitor Kazal-type 7 [Equus caballus] |
| 77.8 | serotransferrin isoform X1 [Equus caballus] |
| 78 | Serotransferrin; Short=Transferrin; AltName: Full=Beta-1 metal-binding globulin; AltName: Full=Siderophilin; Flags: Precursor |
| | serpin B11 [Equus caballus] |
| 68.6 | Serum albumin; AltName: Allergen=Equ c 3; Flags: Precursor |
| | small integral membrane protein 5-like isoform X4 [Equus caballus] |
| 27.5 | stanniocalcin-1 [Equus caballus] |
| 19.2 | superoxide dismutase 3, extracellular, partial [Equus caballus] |
| 37.5 | tartrate-resistant acid phosphatase type 5 isoform X3 [Equus caballus] |
| 23.3 | tetraspanin-1 [Equus caballus] |
| 25.8 | tetraspanin-1-like protein [Equus caballus] |
| 129.5 | thrombospondin-1 [Equus caballus] |
| 17.9 | thy-1 membrane glycoprotein [Equus caballus] |
| 63.9 | tissue-type plasminogen activator isoform 1 [Equus caballus] |
| 21.3 | transferrin, partial [Equus caballus] |
| | transforming growth factor-beta-induced protein ig-h3, partial [Equus caballus] |
| 34.3 | ubiquitin [Equus caballus] |
| 14.7 | ubiquitin A-52 residue ribosomal protein fusion product 1 isoform X2 [Equus caballus] |
| 18 | ubiquitin-40S ribosomal protein S27a [Equus caballus] |
| 39.9 | uncharacterized protein LOC100053897 [Equus caballus] |
| 23.8 | uncharacterized protein LOC100068166 [Equus caballus] |
| 36.5 | unnamed protein product [Equus caballus] |
| 33.6 | unnamed protein product, partial [Equus caballus] |
| | UPF0764 protein C16orf89 homolog [Equus caballus] |
| 13.6 | uterine serpin, partial [Equus caballus] |
| 20.8 | Uterocalin; AltName: Full=Concepticalin; AltName: Full=Equicalin; AltName: Full=Lipocalin P19; Flags: Precursor |
| 9.6 | uteroglobin precursor [Equus caballus] |
| 9.7 | Uteroglobin; AltName: Full=Secretoglobin family 1A member 1; Flags: Precursor |
| 12.2 | uteroglobin-like [Equus caballus] |
| 9.6 | uteroglobin-like precursor [Equus caballus] |
| 58 | vascular non-inflammatory molecule 2 isoform X3 [Equus caballus] |
| 57.5 | vascular non-inflammatory molecule 3-like isoform X1 [Equus caballus] |
| 48.8 | vascular non-inflammatory molecule 3-like isoform X2 [Equus caballus] |
| 21.5 | vitelline membrane outer layer protein 1 homolog isoform X1 [Equus caballus] |
| 17 | vitelline membrane outer layer protein 1 homolog isoform X2 [Equus caballus] |
| 12.9 | WAP four-disulfide core domain protein 2 [Equus caballus] |
| | zinc finger CCCH domain-containing protein 11A isoform X3 [Equus caballus] |
| | zinc finger CCCH domain-containing protein 11A isoform X2 [Equus caballus] |
| | zinc finger CCCH domain-containing protein 11A isoformX1 [Equus caballus] |
| 109.4 | zinc finger protein 280D [Equus caballus] |

FIG. 7E

METHODS AND ARTICLES OF MANUFACTURE FOR ANIMAL THERAPEUTICS

CROSS-REFERENCE TO RELATED APPLICATIONS

This application claims priority to, and the benefit of, U.S. Provisional Patent Application No. 63/341,363, filed May 12, 2022 and titled "METHODS AND ARTICLES OF MANUFACTURE FOR ANIMAL THERAPEUTICS," which is incorporated by reference herein in its entirety for all purposes.

FIELD

This disclosure provides processed fetal tissues, cells, and/or other animal derived materials suitable for therapeutic uses, for example, modulating immune response to infectious disease and supporting repair of tissues damaged by infectious and/or inflammatory disease.

BACKGROUND

Animals are subject to contracting infectious disease, which may result in illness, short-term disability, long-term disability, and/or mortality. Therapeutics (including biologics) for preventing and/or treating animals having infectious disease are thus desirable to decrease risk of animal morbidity and mortality. Though antibiotics exist, overuse of antibiotics has been associated with drug-resistant bacterial strains. Though vaccines and antimicrobial pharmaceutical medications exist, there are certain viral, bacterial, fungal, protozoal, and vector-borne diseases that do not have adequate therapeutics and/or vaccines available. Moreover, vaccines may not be effective in all animals (e.g., young animals, older animals, immunocompromised, and/or highly stressed animals), against immunomodulatory microbes or against microbes capable of frequent mutations. In addition, the body can initiate uncontrolled inflammation in an effort to eliminate an infectious agent (or even against its own tissues) that results in tissue or organ damage which is often difficult for the body to constitutively repair on its own.

Literature suggests that birth (i.e. amnionic, umbilical cord, and cervical mucus plug) tissues may provide, antimicrobial properties, specific upregulation of important innate and adaptive immune responses necessary, modulate the inflammatory response via downregulation of exuberant innate and adaptive immune responses in addition to providing anti-inflammatory components, promote angiogenesis, induce endogenous stem cells to differentiate, induce key signaling through cytokines, chemokines, and growth factors, provide building blocks (i.e. extracellular matrix components), and reduce scarring, which may promote healing of damaged tissues, enhance immune response to infectious disease, and promote an anti-tumor effect.

SUMMARY

In various embodiments, an article of manufacture is provided comprising a dried particulate mixture of amniotic material and a powdered, lyophilized mixture of cervical mucus plug.

In various embodiments, a method is provided comprising dehydrating cervical mucus plug, cryomilling the lyophilized cervical mucus plug, dehydrating amniotic material, cryofractionating the decellularized amniotic material to form a dried particulate mixture of amniotic material, and combining the dried particulate mixture of amniotic material with the ground, lyophilized cervical mucus plug to form a medicament.

The method further comprising administering a third effective amount of the article of manufacture to the animal subject in need thereof at least twenty-four hours after the administration of the second effective amount of the article of manufacture.

The method wherein the animal subject is at least one of dog, a horse, a feline, a ruminant, a reptile, a fish, or a raccoon.

A method of prophylactic medicament administration upon an animal comprising:
  administering an effective amount of the article of manufacture to an animal subject exposed to at least one of an infectious pathogen or becoming infected with a pathogen.

The method further comprising administering a second effective amount of the article of manufacture to the animal subject at least seventy-two hours after the administration of the effective amount of the article of manufacture.

A method of prophylactic medicament administration upon an animal comprising:
  administering an effective amount of the article of manufacture to an animal subject; and
  administering a second effective amount of the article of manufacture to the animal subject at least six months after the administration of the effective amount of the article of manufacture.

A method of medicament administration upon an animal comprising:
  administering an effective amount of the article of manufacture to an animal subject in need of treatment of at least one of an autoimmune disorder and cancer.

A method of medicament administration upon an animal comprising:
  administering an effective amount of the article of manufacture to an animal subject in need of treatment of modulation of aberrant and exuberant inflammation.

A method of medicament administration upon an animal comprising:
  administering an effective amount of the article of manufacture of to an animal subject via a route of administration comprising at least one of intravenous, subcutaneous, intrathecal, topical, transdermal, or nebulization.

A method of medicament administration upon an animal comprising:
  administering an effective amount of the article of manufacture to an animal subject via a route of administration comprising at least one of intravenous, subcutaneous, intrathecal, topical, transdermal, or nebulization.

Utilize the regenerative properties of the allograft in addition to ablating infectious disease to heal pathology associated with infectious disease and restore normal tissue anatomy and function.

BRIEF DESCRIPTION OF THE DRAWINGS

The subject matter of the present disclosure is particularly pointed out and distinctly claimed in the concluding portion of the specification. A more complete understanding of the present disclosure, however, may best be obtained by referring to the following detailed description and claims in connection with the following drawings. While the drawings illustrate various embodiments employing the principles described herein, the drawings do not limit the scope of the claims.

FIGS. 1, 2A, and 2B illustrate cytokine presence in various birth tissues as detected by antibody microarray assay, in accordance with various embodiments.

FIGs. 7A, 7B, 7C, 7D, and 7E illustrate an assay that illustrates proteins present in CMP.

DETAILED DESCRIPTION

Definitions

Figure 3:
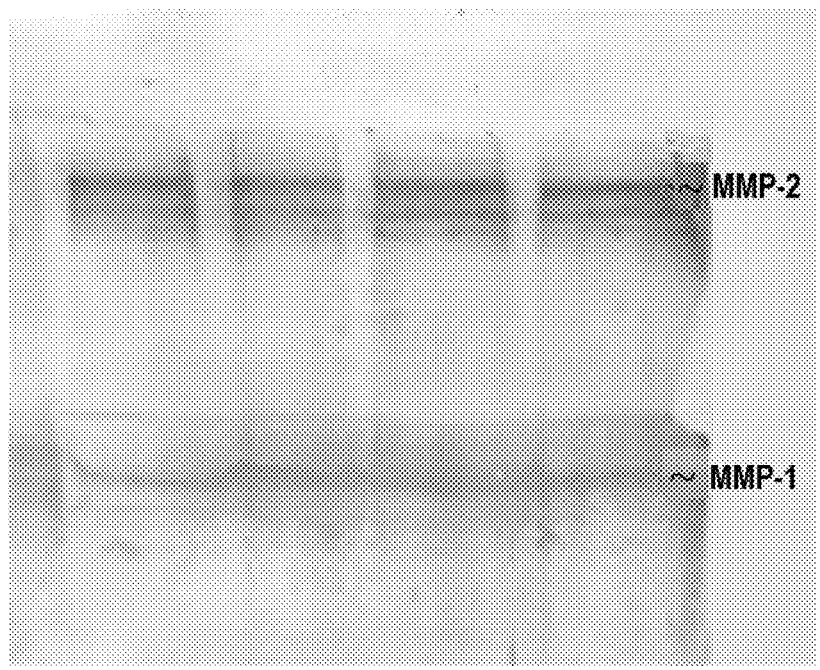
FIGS. 3, 4 and 5 illustrate Western blots and a zymogram that show the presence of certain proteins and enzyme activities in fetal tissues, in accordance with various embodiments.

The term "about" or "approximately" means within 5% of a given value or range.

As used herein, the term "isolated cell" refers to a cell that has been removed from its in vivo location.

As used herein, the term "decellularization" refers to a process that removes cells from a tissue while preserving the native superstructure and composition of the extracellular matrix (ECM). For example, decellularization may comprise a dehydrating process followed by a cryofracture to break apart membranes of cells while preserving cellular components which are important in healing. In various embodiments, an amnion particulate mixture can be obtained by decellularizing a fetal tissue comprising amnion. There are a number of methods of decellularization of tissue known in the art, including, but not limited to, chemical agents, hypotonic and hypertonic solutions, detergents (e.g., Triton-X), alcohols, solvents (e.g., tributyl phosphate (TBP)), biologic agents (e.g., collagenase, trypsin, lipase, nucleases, α-galactosidase), non-enzymatic agents (e.g., chelating agents such as EDTA or EGTA), physical agents (e.g., temperature, force and pressure, mechanical methods, non-thermal irreversible electroporation (NTIRE)) (see, for example, Crapo et al., Biomaterials. 2011; 32(12): 3233-3243). In various embodiments, one or a combination of the aforementioned methods may be used to decellularize a tissue. However, methods that preserve the complex composition and three-dimensional ultrastructure of the extracellular matrix (ECM) are preferred. In various embodiments, a tissue can be decellularized via dehydration or -mechanically decellularized, e.g., by cryofractionation, a procedure in which a tissue is frozen and ground in a cryomill to produce a mixture of particles. Such particles are obtained from the cryofractionation of about 0.5 $cm^2$, or about 1 $cm^2$, or about 1.5 $cm^2$, or about 2 $cm^2$, or about 2.5 $cm^2$, or about 3 $cm^2$, or about 3.5 $cm^2$ or about 4 $cm^2$, or about 4.5 $cm^2$ to about 5 $cm^2$ of amnion or more. The amnion can have a thickness of from about 500 µm to 50 µm, or from 400 µm to about 50 µm, or from about 300 µm to 50 µm, or from about 200 µm to about 50 µm, or from about 150 µm to about 50 µm, from about 100 µm to about 50 µm or from about 50 µm to about 25 µm or less. In another embodiment, the amnion has a thickness of about 500 µm, or about 400 µm, or about 300 µm, or about 200 µm, or about 150 µm, or about 100 µm, or about 50 µm, or about 25 µm or less.

The term "amnion" refers to a thin, cellular, extra-embryonic membrane that forms the inner membrane of a closed sac surrounding and protecting an embryo in reptiles, birds, and mammals. The sac contains the fetus and amniotic fluid, in which the embryo is immersed, cushioned, nourished and protected. Typically, the amnion is a tough, transparent, nerve-free, and minimally vascularized membrane consisting of two layers of cells: an inner, single-cell-thick layer of ectodermal epithelium and an outer covering of mesodermal, connective, and specialized smooth muscular tissue. In the later stages of pregnancy, the amnion expands to come in contact with the inner wall of the chorion creating the appearance of a thin wall of the sac extending from the margin of the placenta. The amnion and chorion are closely applied, though not fused, to one another and to the wall of the uterus. Thus, at the later stage of gestation, the fetal membranes are composed of two principal layers: the outer chorion that is in contact with maternal cells and the inner amnion that is bathed by amniotic fluid. The amnion has multiple functions, e.g., as a covering epithelium, as an active secretory epithelium, and a conductive medium for soluble messenger molecules, nutrients, and metabolic building blocks.

Though the chorion may have healing benefits, but may not be a desirable fetal tissue to be used as a xenograft, because unlike the amnionic membrane, it may not be immune privileged due to the particular placental structure found in equids (i.e. diffuse epithelialchorial & miccrocotyledonary), which is different from the human placenta. Though use of chorion is contemplated in various embodiments disclosed herein, equine chorion and bovine chorion may be present in various embodiments.

As used herein, the term "tissue" refers to an aggregate of similar cells and associated extracellular matrix (ECM) forming a definite kind of organized material with a specific function, in a multicellular organism.

As used herein, an "amnion tissue" refers to the isolated cellular, extra-embryonic amnion membrane that is detached from the chorion. In various embodiments, the amnion tissue is air-dried. In various embodiments, the amnion is air-dried for about 60 to about 90 minutes or more at ambient temperature (i.e. about 18 to 24° C.).

As used herein, a "particulate mixture" refers to the powder or particles obtained from the cryofractionation or cryofracture of dehydrated amnionic membrane and/or lyophilized amniotic fluid.

As used herein, the term "fetal tissue" refers to extra-embryonic tissues including, but not limited to, amnion, chorion, yolk sac, the allantois, umbilical cord and/or fetal placenta (villous chorion), and cervical mucus plug.

As used herein, the term "fetal cells" refers to cells resident in the extra-embryonic tissues including, but not limited to, amnion, chorion, yolk sac, the allantois, umbilical cord, fetal placenta (villous chorion) and/or amniotic fluid. In various embodiments, the term "fetal cells" refer to isolated fetal cells. In various embodiments, the term "fetal cells" refers to unfractionated cells of the amniotic fluid including epithelial and/or amniotic fluid or membrane-derived mesenchymal stem cells.

As used herein, "amniotic material" refers to a composition comprising at least one of amnion, amnionic fluid, or preparations thereof.

The term "promoting healing" refers to causing a favorable result compared to no treatment. The favorable result comprises any one or more of the following such as reduction of scarring, modulation of inflammation, regrowth of normal tissue or growth of scar tissue, improved load bearing on a limb movement, closure of wound, reduction in infection and reduction in mortality associated with the underlying pathology.

The term "compatible with a recipient animal" denotes the origin of the tissue as being from the same species or closely related species (i.e. allogeneic) or different species (i.e. xenogeneic).

The term "xenogeneic" infers compatibility of tissues or cells from donor animals belonging to individuals of different species than the recipient animals.

The term "allogeneic" infers tissues or cells that are genetically dissimilar although from individuals of the same species but compatible with recipients from the same species.

The term "antiviral support" means supporting a broad array of antimicrobial effects on virus infections and associated sequelae in numerous species.

The term "immunomodulatory" means appropriately balancing the pro-inflammatory with anti-inflammatory mechanisms used by the immune system to effectively fight off infections and prevent cancer, as well as manage chronic or degenerative conditions, but not to the detriment of the organism or of healing.

The term "aberrant or exuberant inflammation" means an abnormal and exaggerated inflammatory response that is uncontrolled and causes damage to the organism.

The term "antibacterial support" means supporting a broad array of antimicrobial effects on bacterial infections and associated sequelae in numerous species.

The term "antimicrobial support" means supporting a broad array of antimicrobial effects on viral and bacterial, viral, fungal, protozoal, and vector-borne infections and associated sequelae in numerous species.

The term "carrier" and/or "suspension agent" means non-toxic materials used in the formulation of a medicament to provide a medium, bulk and/or useable form to a medicament. A carrier may comprise one or more of such materials such as an excipient, stabilizer, or an aqueous pH buffered solution. Examples of physiologically acceptable carriers include aqueous or solid buffer ingredients including phosphate, citrate, and other organic acids; antioxidants including ascorbic acid; low molecular weight (less than about 10 residues) polypeptide; proteins, such as serum albumin, gelatin, or immunoglobulins; hydrophilic polymers such as polyvinylpyrrolidone; amino acids such as glycine, glutamine, asparagine, arginine or lysine; monosaccharides, disaccharides, and other carbohydrates including glucose, mannose, or dextrins; chelating agents such as EDTA; sugar alcohols such as mannitol or sorbitol; glycosaminoglycans such as hyaluronic acid; salt-forming counter ions such as sodium; and/or nonionic surfactants such as polysorbate 20 (e.g., TWEEN), polyethylene glycol (PEG), and poloxamers such as PLURONICS.

As used herein, an "animal" refers to living multi-cellular vertebrate organisms, a category that includes, for example, mammals, birds, reptiles, and amphibians. The term mammal includes both human and non-human mammals. Similarly, the term "subject animal" includes both human and non-human subjects. The term "subject animal" refers to an individual human or animal which has a site of injury or disease.

As used herein, a non-human animal can refer to a mammal including, but not limited to, a domesticated animal such as a dog, a racing dog, sheep, a pig, a goat, cattle or other ruminant, a zebu, a cat, a guinea pig, a donkey, water buffalo, including "river buffalo" and "swamp buffalo", a horse, a racing horse, a dromedary camel, a yak, a raccoon, bactrian camel, a llama, an alpaca, a ferret, a mouse, a bali cattle, a gayal, a rabbit, a rat and a lab rat, a silver fox or a hedgehog.

In various embodiments, a non-human animal can refer to mammals kept in zoos including, but not limited to, zebra, gazelle, wolves, wild swine (pigs & hogs), wild cattle, warthogs, vervet monkeys, two-toed sloths, tree pangolins, tigers, tapirs, tamandua or lesser anteaters, takins, sun bears, striped hyena, spotted hyena, spiral-horned antelope, somali wild ass, snow leopards, small cats, sloth bears, singing dogs, siamang, serval, sea lions, rock hyrax, rhinoceros, reindeer, red pandas, pygmy marmosets, pygmy hippopotamus, przewalski's horses, pronghorns, prairie dogs, porcupines, polar bears, painted dogs, otters, oryx, orangutan, okapi, ocelot, nubian ibex, nile lechwe, naked mole-rats, mountain lions(puma, cougar), monkeys, meerkat, mangabey, mandrill, lynx and bobcats, lions, leopards, lemur, jaguars, honey badgers (ratel), hippos, hamadryas baboons, guenon, guanaco, gorillas, giraffe, giant pandas, giant anteaters, gelada baboons, fossa, fishing cats, elephants, echidna, dhole, coquerel's sifaka, clouded leopards, chimpanzees, cheetahs, tigers, caracals, capybara, camels, brown bears, bonobos, binturongs, bat-eared fox, bats, armadillos, antelope, andean (spectacled) bears and agouti.

In various embodiments, a non-human animal can refer to mammals considered by the World Wildlife Fund to be endangered including, but not limited to, the amur leopard, black rhino, cross river gorilla, javan rhino, mountain gorilla, pangolin, saola, south china tiger, sumatran elephant, sumatran orangutan, sumatran rhino, sumatran tiger, vaquita, western lowland gorilla, yangtze finless porpoise, african wild dog, amur tiger, asian elephant, bengal tiger, black spider monkey, black-footed ferret, blue whale, bonobo, bornean orangutan, borneo pygmy elephant, chimpanzee, eastern lowland gorilla, fin whale, ganges river dolphin, giant panda, hector's dolphin, indian elephant, indochinese tiger, indus river dolphin, malayan tiger, north atlantic right whale, orangutan, sea lions, sei whale, snow leopard, Sri Lankan elephant, tigers and whales.

In various embodiments, a non-human animal can refer to marsupials, including, but not limited to, wallabies, koalas, possums, opossums, kangaroos, bandicoots, wombats, bettongs, bilbys, quolls, quokkas and the Tasmanian devil.

The term "pharmaceutical excipients" refers to non-toxic adjuvants or compounds which can be added to various embodiments which are capable of enhancing the biologically active effects of the peptide or its absorbency in the body. This includes, for the avoidance of doubt, suspending agents such as polyethylene glycol or PEG, as well as hyaluronic acid, and others.

The term "effective amount" or "therapeutically effective amount" means that amount of a medicament that will elicit the biological or medical response of a subject that is being sought by a medical doctor or other clinician.

The term "reconstituted" means that that a carrier is added to the medicament. For example, a liquid carrier for reconstitution may comprise a biocompatible solution such as normal saline, e.g. phosphate buffered saline (PBS) or amniotic fluid. A liquid carrier for reconstitution may comprise, in various embodiments, calcium-free sterile, non-pyrogenic isotonic solution suitable for intravenous or subcutaneous administration. For example, without limitation, one such liquid carrier is sold under the trademark PlasmaLyte A™ in a single dose container for intravenous administration. Each 100 mL of PlasmaLyte A contains 526 mg of Sodium Chloride, USP (NaCl); 502 mg of Sodium Gluconate ($C_6H_{11}NaO_7$); 368 mg of Sodium Acetate Trihydrate, USP ($C_2H_3NaO_2·3H_2O$); 37 mg of Potassium Chloride, USP (KCl); and 30 mg of Magnesium Chloride, USP (MgCl$_2$·6H$_2$O). PlasmaLyte A contains no antimicrobial agents. The pH is 7.4.

The term "administering" means applying or injecting or ingesting the medicament. The term "applying" is used broadly and includes uses such as biological membrane bandage, washes, infusions, and implantation.

As used herein, the term "parvovirus" includes any member of the family Parvoviridae, including, but not limited to, any member of the Protoparvovirus genus, including carnivore protoparvovirus virus. The term "parvovirus" further includes naturally-occurring (e.g., wild-type) parvovirus; naturally-occurring parvovirus variants; and parvovirus variants generated in the laboratory, including variants generated by selection, variants generated by chemical modification, and genetically modified variants (e.g., parvovirus modified in a laboratory by recombinant DNA methods).

Amnion is an abundant source of collagen, laminin, and fibronectin, as well as the other extracelluar matrix proteins, carbohydrates, lipids, hyaluronic acid, proteoglycans, glycoproteins, pluripotent mesenchymal stem cells (MSC) and epithelial stem cells (ESC), antimicrobial factors (defensins, lysozyme, lactoferrin, elafin, secretory leukocyte protease inhibitor, cathelicidin, cytostatin, LL-37), chemokines, cytokines (i.e. IL-8, IFN-γ, TNF-α, IL-6, IL-10, IL-1RA), complex growth factors (i.e. VEGF, PDGF, bFGF, KGF, IGFBPs, NT, TGF-β, HGF, EGF), anti-inflammatory proteins (MIF, TIMP), small molecular weight mediators (lysine, taurine, alpha-aminoadipic acid, spermidine), and secretome (exosomes and extracellular vesicles that contain a wide range of bioactive molecules including nucleic acids (miRNA, mRNA), lipids, and proteins, and others that are essential for fetal growth, development, and protection. In particular, amnion has a complete lack of surface antigens, thus it does not induce an immune response when implanted into a "foreign" body, which is in contrast to most other allograft implants. Furthermore, amnion has a broad spectrum of antimicrobial activity against bacteria, fungi, protozoa, and viruses for reduced risk of post-operative infection, infected joints, resistantly infected wounds, post-operative infections, and prevention of infectious disease. The potential of amnion to treat various disease states is large. See, for example, Elkhenany H, et al. (2022) Stem Cell Res Ther 13:8, available at https://doi.org/10.1186/s13287-021-02684-0, which is hereby incorporated by reference in its entirety for all purposes.

A "kit" is an assembly of parts, materials, and compositions of matter packaged together to facilitate a treatment. Kits commonly comprise instructions for the use of the parts, materials and compositions.

The term "cervical mucus plug" or "CMP" means mucus found in or near the cervix of a mammal. The CMP may be collected from a mammal that is pregnant or has given birth recently (within one week). However, the CMP may be collected at other times from female mammals, whether or not they are, may become, or recently were, pregnant.

The term "cervical mucus plug-derived" or "CMP derived" means a material derived from CMP.

The term "medicament" means a composition used for medical treatment. The composition may comprise a single material or a formulation of various materials configured for administration to a subject.

The term "allograft" means a tissue graft or other tissue containing material from a donor of the same species as the recipient but not genetically identical.

The term "xenograft" means a tissue graft or other tissue containing material from a donor of a different species as the recipient.

Amniotic material is immune-privileged and well suited for regenerative medicine applications. Amniotic material provides various beneficial properties that make it a compelling candidate treatment for disease intervention, including anti-microbial effects, enhanced angiogenesis, modulation of inflammation, reduction of fibroblast/scar tissue formation and promotion of normal tissue regeneration and repair via endogenous stem cell recruitment and utilization of ECM building blocks.

Moreover, amniotic material combined with CMP-derived material, in various embodiments, provides enhanced anti-microbial effects, among others. In various embodiments, medicaments disclosed herein include amniotic material. The amniotic material may be animal-derived and, in particular, may be mammal-derived. Amniotic material may be collected during or shortly after the birthing process. Amniotic material may then be processed by various methods, for example, amnionic material may undergo a decellularization process to form a powdered, decellularized material. This powdered, decellularized material comprises ECM comprising, for example, collagens, laminins, hyaluronic acid, proteoglycan, glycosaminoglycans (GAGs), and fibronectin, as well as antimicrobial factors, anti-fibrotic factors, anti-inflammatory factors, growth factors and signaling molecules including cytokines, interleukins, chemokines, prostaglandins, exosomes, and extracellular vesicles and their contents (i.e. mRNA, miRNa), and cellular receptor ligands. Amniotic material has been shown to be able to manage inflammation and promote tissue regeneration and angiogenesis without scarring.

In various embodiments, medicaments disclosed herein include CMP. CMP may be processed to form a powdered, dried form, as described below. CMP has been shown to exhibit anti-microbial activity and to possess an immunomodulatory ability. CMP comprises, for example, mucins (glycoproteins, including MUC5B and MUC7), matrix metalloproteases (MMPs) and TIMPs (cognate inhibitors of MMPs) and cytokines. In particular, Interleukin-15 (IL-15) is found in significant concentrations in CMP. Various mucins found in CMP also exhibit anti-microbial properties. Other components include: complement proteins, antimicrobial peptides (elafin, lysozyme, defensins, lactoferrin, secretory leukocyte protease inhibitor, cathelicidins), immunoglobulins, chemokines, acute phase proteins (haptoglobin, serum amyloid A, alpha1-acid glycoprotein), anti-inflammatory molecules (IL-10, alpha-2 macroglobulin), and others. See more specific equine CMP components in the associated tables (FIGs. 7A, 7B, 7C, 7D, and 7E) for a more complete list of molecules, classes and functions. Some components and actions overlap that of amnion.

In various embodiments, umbilical cord material, is lyophilized (i.e., freeze-dried) and ground into a powdered form. In various embodiments, umbilical cord material is otherwise dried or desiccated. Dehydrating and cryomilling (e.g., decellularization) is an effective method for preserving, for example, the quaternary and tertiary structure of proteins in the material being lyophilized while also imparting shelf stability. Umbilical cord material, as described herein, is a source of various biologically active proteins and thus lyophilization may be used to retain tissue structure and protein integrity during processing.

In various embodiments, CMP is dehydrated or lyophilized (i.e., freeze-dried) and ground into a powdered form. In various embodiments, CMP is otherwise dried (dehydrated) or desiccated. Lyophilization is an effective method for preserving, for example, the quaternary and tertiary structure of proteins in the material being lyophilized while also imparting shelf stability. CMP, as described herein, is a source of various biologically active proteins and thus lyophilization may be used to retain tissue structure and protein integrity during processing.

Medicaments in accordance with various embodiments further comprise, lyophilized amniotic fluid. Medicaments in accordance with various embodiments further comprise lyophilized amniotic tissue fluid. Medicaments in accordance with various embodiments may be in reconstituted form. In this regard, pharmaceutically acceptable aqueous solutions (i.e., pharmaceutically acceptable carriers and/or pharmaceutically acceptable excipients) may be mixed with lyophilized CMP and decellularized amniotic material.

Medicaments in accordance with various embodiments may comprise lyophilized CMP and decellularized amniotic material derived from the same species, the same genus, and/or the same family. However, in various embodiments, the lyophilized CMP and decellularized amniotic material are derived from different species, different genera, and/or different families. Moreover, the subject to which the medicament is administered may be of the same species, the same genus, and/or the same family as the lyophilized CMP and dried particulate mixture of amniotic material. However, in various embodiments, the subject to which the medicament is administered may be of a different species, different genera, and/or different family from that which the lyophilized CMP and dried particulate mixture of amniotic material are derived.

Medicaments in accordance with various embodiments may comprise lyophilized CMP and dried particulate mixture of amniotic material in any suitable weight ratio, excluding any pharmaceutically acceptable carrier or excipients. In various embodiments, a medicament comprises from 1% by total weight lyophilized CMP and 99% by total weight dried particulate mixture of amniotic material to 1% by total weight dried particulate mixture of amniotic material and 99% by total weight lyophilized CMP. In various embodiments, a medicament comprises from 20% by total weight lyophilized CMP and 80% by total weight dried particulate mixture of amniotic material to 20% by total weight dried particulate mixture of amniotic material and 80% by total weight lyophilized CMP. In various embodiments, a medicament comprises from 40% by total weight lyophilized CMP and 60% by total weight dried particulate mixture of amniotic material to 40% by total weight dried particulate mixture of amniotic material and 60% by total weight lyophilized CMP. In various embodiments, a medicament comprises from 5:1 ratio of lyophilized CMP to dried particulate mixture of amniotic material to a 1:5 ratio of lyophilized CMP to dried particulate mixture of amniotic material. In various embodiments, a medicament comprises a 1:1 ratio of lyophilized CMP to dried particulate mixture of amniotic material. In various embodiments, a medicament comprises a 1:2 ratio of lyophilized CMP to dried particulate mixture of amniotic material. Medicaments in accordance with various embodiments may further comprise lyophilized umbilical cord and placental material.

While not desirous of being bound by theory, it is believed that there is a synergistic anti-microbial effect to be observed between the lyophilized CMP and the dried particulate mixture of amniotic material. Addition of lyophilized CMP adds anti-inflammatory effects (i.e. α-macroglobulin and others), strong anti-microbial and, especially, anti-viral effects (IL-15, INF-α, β-defensins, macrophage inhibitory protein (MIP)), which may lead to more quickly stopping viral replication, viral shedding, and naturally enhance the immune response of a subject. While not desirous of being bound by theory, it is believed that lyophilized CMP adds significant amounts of Interleukin, and in particular Interleukin-15, as well as mucins, such as MUC1, which is believed to prevent transmission of various viruses. It is believed that a combination of lyophilized CMP and the dried particulate mixture of amniotic material interferes with virus-associated (or microbial-associated) trauma and tissue damage (e.g., ischemic, inflammatory, etc.) by modulating the infection and aberrant and exuberant inflammation, followed by helping and accelerating host mechanisms to repair tissue and restore tissue architecture and function more effectively than amnion alone. Moreover, it is believed that a combination of lyophilized CMP and the dried particulate mixture of amniotic material provides enhanced prevention of viral entry and replication, latent states, viremia, secondary tissue infection, and microbial-related tissue damage, as well as similar levels of enhancement in healing the damaged tissue and strengthening long-term immunity more than amnion alone. All other effects, including tissue protective effects, prevention of apoptosis of target cells in the tissue to be healed, and preventing dysregulation of exuberant inflammation as well as coagulation, promotion of host stem cell recruitment and proliferation of stem cells, cytokines, chemokines, and necessary growth factors, paracrine effects through exosomes/secretome for intercellular communication necessary for the antimicrobial, anti-inflammatory, and regenerative effects will also be enhanced.

It should be noted that, in accordance with various embodiments, medicaments comprising lyophilized CMP and dried particulate mixture of amniotic material encompass medicaments comprising lyophilized CMP and dried particulate mixture of amniotic material. Together, medicaments comprising lyophilized CMP and dried particulate mixture of amniotic material form at least one of an allograft or a xenograft, depending upon the recipient subject.

Preparation of Dried Particulate Mixture of Amniotic Material

Amniotic material may be obtained from a horse shortly after giving birth. In various embodiments, the amniotic material is subject to dehydration in room air under a sterile hood after being flattened, stretched, layered with mesh, and stacked on drying racks to dry for 24 hours or lyophilization. In that regard, amniotic material can be introduced into a lyophilizer. The lyophilizer rapidly freezes the amniotic material. Then, the pressure inside the lyophilizer is lowered while heat is added. The subsequent dehydrated or freeze-dried amniotic material is removed from the lyophilizer and subject to milling, for example, cryofractionation as described above. For the avoidance of doubt, it is noted that cryofracture is not to be construed as cryopreservation. Cryofractionation comprises cooling the membrane while cryofracturing/milling, which allows particles to break apart to form functional proteins/molecules with antiviral, healing, and immune modulating/anti-inflammatory functions. However, in various embodiments, amniotic material is subject to cryofracture. In this manner, previously lyophilized amniotic material is frozen quickly with a cold material, such as liquid nitrogen. Then, the frozen amniotic material is subject to a mechanical shock (i.e. magnetic hammer mill vs ball mill) that fractures the amniotic material structure. The fractured amniotic material may then be subject to cryofractionation or grinding as described above. In various embodiments, however, the amniotic material is not subject to lyophilization. In such embodiments, the amniotic material is dried (i.e., dehydrated) and then cryofractionated as described herein.

The cryofractionated or cryofractured amniotic material is ground to obtain a powder of relatively uniform particles size. For example, the cryofractionated or cryofractured amniotic material may be ground to a particle uniformity of 90% of particles being below 70 microns in diameter, a particle uniformity of 95% of particles being below 70 microns in diameter, and/or a particle uniformity of 99% of particles being below 70 microns in diameter. In various embodiments, the cryofractionated or cryofractured amniotic material is ground to obtain a powder including various particle sizes as well. Thus, a dried particulate mixture of amniotic material is obtained. The resulting cryomilled particulate mixture is then dry filtered to include the desired range of particle sizes for an intended application.

Filtration of amniotic material may proceed in dry form. In that regard, a vortexer may be used to agitate the amniotic material and force the amniotic material through one or more membranes or meshes to yield a filtrate (the filtered particles having a more uniform size) and a retentate, an unfiltered portion that did not pass through the membrane or mesh.

In various embodiments, for example for use in subcutaneous administration formulation, particle size uniformity is of less importance than, for example, intravenous administration formulations. In that regard, in various embodiments, the cryofractionated or cryofractured amniotic material may be ground to a particle uniformity of 90% of particles being below 500 microns in diameter, a particle uniformity of 95% of particles being below 500 microns in diameter, and/or a particle uniformity of 99% of particles being below 500 microns in diameter. Moreover, in various embodiments, cryofractionated or cryofractured amniotic material may be produced so that a particle uniformity of 95% of particles being between 70 microns and 500 microns in diameter is obtained. Further, in various embodiments, cryofractionated or cryofractured amniotic material may be produced so that a particle uniformity of 95% of particles being between 40 microns and 100 microns in diameter is obtained. Various size separation methodologies may be employed to achieve more discrete particle sizes. Thus, a dried particulate mixture of amniotic material is obtained.

Preparation of CMP

CMP may be obtained from a horse shortly after giving birth. In various embodiments, the CMP is subject to lyophilization. In that regard, CMP is introduced into a lyophilizer. The lyophilizer rapidly freezes the CMP. Then, the pressure inside the lyophilizer is lowered while heat is added. The subsequent freeze-dried CMP is removed from the lyophilizer and subject to milling, for example, cryofractionation as described above. However, in various embodiments, CMP is subject to cryofracture. In this manner, CMP is frozen quickly with a cold material, such as liquid nitrogen. Then, the frozen CMP is subject to a mechanical shock that fractures the CMP structure. The fractured CMP may then be subject to cryofractionation or grinding as described above.

The cryofractionated or cryofractured CMP is ground to obtain a powder of relatively uniform particles size. For example, the cryofractionated or cryofractured CMP may be ground to a particle uniformity of 90% of particles being below 70 microns in diameter, a particle uniformity of 95% of particles being below 70 microns in diameter, and/or a particle uniformity of 99% of particles being below 70 microns in diameter. For a further example, the cryofractionated or cryofractured CMP may be ground to a particle uniformity of 90% of particles being below 100 microns in diameter, a particle uniformity of 95% of particles being below 100 microns in diameter, and/or a particle uniformity of 99% of particles being below 100 microns in diameter. Thus, powdered, lyophilized CMP is obtained.

Filtration of CMP may proceed in dry form. In that regard, a vortexer may be used to agitate the CMP and force the CMP through one or more membranes or meshes to yield a filtrate (the filtered particles having a more uniform size) and a retentate, an unfiltered portion that did not pass through the membrane or mesh. The retentates of CMP and amnion material, which may be >70 micron in particle size and too large for intravenous administration, may be applied to a wrap or other substrate for topical placement onto a wound, lesion, or other exterior of a subject animal.

The filtrate of CMP and amnion material, which may be <70 micron in particle size, may further be added to a buffered solution and used an ophthalmic preparation for administration into the eye of a subject animal. In addition, tarsorrhaphy for 3-10 days post-application may also be performed.

In various embodiments, for example for use in subcutaneous administration formulation, particle size uniformity is of less importance than, for example, intravenous administration formulations. In that regard, in various embodiments, the cryofractionated or cryofractured CMP may be ground to a particle uniformity of 90% of particles being below 500 microns in diameter, a particle uniformity of 95% of particles being below 500 microns in diameter, and/or a particle uniformity of 99% of particles being below 500 microns in diameter. Moreover, in various embodiments, cryofractionated or cryofractured CMP may be produced so that a particle uniformity of 95% of particles being between 70 microns and 500 microns in diameter is obtained. In various embodiments, powdered, lyophilized CMP is filtered to select for particle size uniformity after cryofractionation. Thus, powdered, lyophilized CMP is obtained for use as a reconstitutable product with greater availability, longer shelf-life, and more convenient storage.

Preparing a Medicament

The powdered, lyophilized CMP may be combined with a dried particulate mixture of amniotic material to form a CMP/amniotic material medicament. Storage of CMP/amniotic material medicament may be achieved by cooling the cells at a cooling rate of 1° C. per minute from 4° C. to −80° C., using a passive cooling controlled-rate freezer, e.g., the CoolCell™ (commercially available from Biocision.) Such storage may be used in liquid formulations only. In various embodiments, however, the lyophilization and cryofractionation employed enable storage without freezing for resuspension at a later time.

The CMP/amniotic material medicament may be reconstituted as described herein by adding a pharmaceutically acceptable carrier and/or pharmaceutically acceptable excipient.

Analysis of CMP

Powdered, lyophilized CMP was prepared as described herein. With reference to FIG. 1, Sample CMP-1 represents lyophilized powder extraction with 4M guanidine-HCl followed by TCA precipitation, and resuspension in 2× Laemmli loading buffer, desalting into 1M Tris-HCl. The CMP-2 sample extraction arose from 6M urea extraction of the guanidine-HCl insoluble pellet, followed by the same treatments. The values in the FIG. 1 are reported in pg/ml and, as noted for IL-4 and IL-15, were converted into pg/mg of starting material, denoted as "S/M" in FIG. 1.

Analysis of CMP/Amniotic Material Medicament

CMP/amniotic material medicament was subjected to guanidine-HCl extraction followed by serial extraction using guanidine-HCl followed by urea extraction. In particular, 1000 mg of CMP/amniotic material medicament was added to 12 mL of 4M guanidine-HCl in a 50-mL conical tube. This was agitated for 1 hour on a laboratory vortexer at room temperature (RT). One-twelfth of the starting material (i.e., 1 mL) of the resulting solution was transferred into a fresh microcentrifuge tube and was centrifuged for 45 minutes at RT. The insoluble pellet was further extracted with urea as described below. The guanidine-extracted supernatant was subjected to trichloroacetic acid (TCA) and acetone precipitation. Briefly, one-fifth (i.e. 200 µL) of guanidine supernatant was combined with 200 µL of TCA and 1600 µL of ice-cold acetone and chilled for 1 hour at −20° C. The samples were centrifuged at 14000×g at RT for 10 min and washed three times with ice-cold 80% acetone. After 5 minutes of air-drying, the pellet was resuspended by trituration in 2× Laemmli sample loading buffer (with beta-mercaptoethanol) and incubated in a 60° C. water bath for 20 minutes. Samples were subjected to buffer swapping into 100 µL of 1M Tris-HCl buffer (pH 6.8) containing 1× Protease Inhibitor Cocktail I (cat #P50600-1, Research Products International, Mt. Prospect IL, USA) by means of EZ-Desalt Spin Desalting Columns (cat. #6564-25, BioVision, Milpitas CA, USA).

The resulting insoluble pellets from guanidine-HCl extraction, as detailed above, were then added to 6M urea, vortexed for an hour, and centrifuged for 10 minutes at RT. This was followed by TCA/acetone precipitation and desalting as described above for guanidine-extracted samples. Final volume was 100 µL 1M Tris-HCl (pH 6.8) containing protease inhibitors.

Controls and dilutions of standards provided in the QuantiBody Equine Cytokine Array 1 (catalog #QAE-CYT-1, RayBiotech, Peachtree Corners GA, USA) were applied to eight different wells on the microarray slide in order to establish standard curves for various analytes.

In the analytical array, dots of capture antibodies for each cytokine were printed onto the glass slide. Samples are loaded into individual wells containing a 48-spot array. If the cytokine is present, it will attach to its corresponding dot. Subsequent incubation with biotinylated detection antibody and fluorescent dye (Cy3)-conjugated streptavidin results in a fluorescent signal that can be quantified when matched against a dilution series of purified protein standards. The completed array was subject to laser scanning analysis and data extraction. Standard curves and calculation of sample concentration were deduced using the QAE-CYT-1 Q-Analyzer software, version 8.10.4.

With reference to FIGS. 2 and 3, various cytokines found in the CMP/amniotic material medicament are shown in pg/ml in FIG. 2 and pg/mg of starting material in FIG. 3. In FIGS. 2 and 3, SA1-SA6 refer to the following:

Sample 1 (SA1): Guanidine-extracted CMP/amniotic material medicament, desalted

Sample 2 (SA2): Guanidine-extracted CMP/amniotic material medicament, TCA-precipitated, desalted Sample 3 (SA3): Urea-extracted CMP/amniotic material medicament, desalted Sample 4 (SA4): Urea-extracted CMP/amniotic material medicament, TCA-precipitated, desalted Sample 5 (SA5): Guanidine-extracted CMP/amniotic material medicament, TCA-precipitated, desalted Sample 6 (SA6): Amniotic Fluid only In that regard, when comparing cytokines detected in CMP/amniotic material medicament using various extraction protocols, some trends become apparent. In most cases, cytokines are lost (e.g. MCP-1, VEGF-A, and IL-Ra) when a TCA precipitation step is included. However, on occasion, some cytokines (IFNg and IL-10) show up in the TCA-precipitated samples whereas they were not initially detected.

It may be concluded that cytokine detection can be highly variable depending on what extraction methods are used.

Fetal tissue is rich in antiviral factors. For example, matrix metalloproteases MMP-2 and MMP-1 and Interleukin IL-15, as well as others described herein, Western blots probed with anti-human MMP-2 and anti-human IL-15 were transferred from denaturing polyacrylamide gel electrophoresis (SDS-PAGE) gels loaded with equine amniotic fluid and extracts from equine placental tissue. Zymography was performed on gelatin-poyacrylamide gels to visualize MMP-2 and other gelatinase/matrix metalloprotease activities in equine amniotic fluid. FIG. 3 illustrates the result of such a Western blot. Here, amniotic fluid was collected during birth of four different healthy foals. The amniotic fluid samples were subjected to SDS-PAGE and transferred to PVDF membrane. Western blot was probed with rabbit primary antibody against human MMP-2 (also known to cross-react with human MMP-1) and anti-rabbit secondary antibody. Samples show immunoreactive bands likely to be MMP-2 (72 kDa) and MMP-1 (54 kDa).

Figure 4:
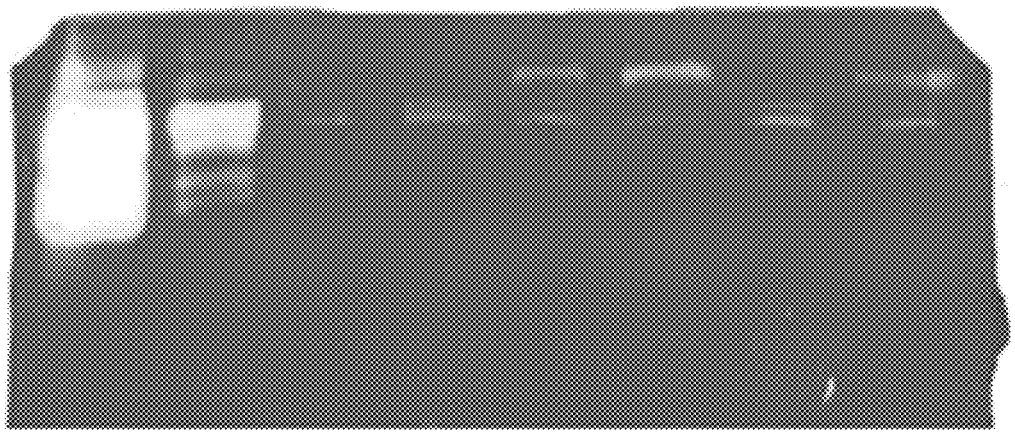

With reference to FIG. 4, a negative stained gelatin/polyacrylamide gel (zymogram) is shown illustrating various forms of active matrix metalloproteinases exhibiting gelatinase activity. Lane 1 shows positive control (*Clostridium histolyticum* Collagenase I), Lane 2 shows fresh equine amniotic fluid, while Lanes 3-8 show various resuspended lyophilized amniotic fluid samples.

Figure 5:
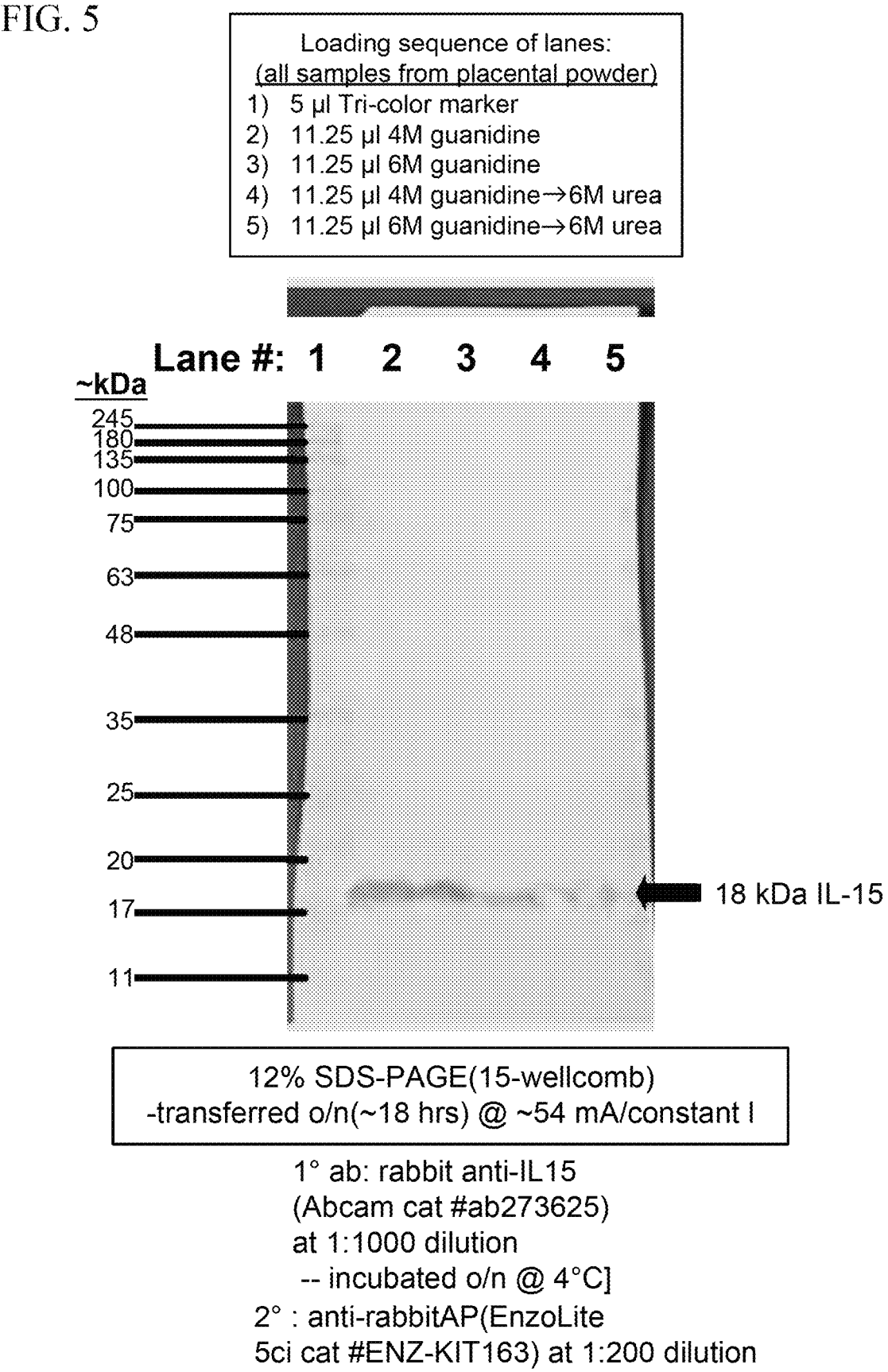

With reference to FIG. 5, a single strong band for IL-15 was visualized by development of alkaline phosphatase (AP)-conjugated secondary antibody. The protein detected is of the appropriate molecular weight (~18 kDa) and illustrates the cross-reactivity of this particular anti-human primary antibody against equine antigens. Techniques used to recover detectable amounts of antigen from lyophilized equine placental tissue include extraction using two different concentrations of guanidine hydrochloride or serial extraction of the insoluble guanidine-HCL pellets with 6 M urea. All samples were precipitated (i.e. desalted) using 10% trichloroacetic acid and linear polyacrylamide (nonproteinaceous carrier) in the presence of 80% cold acetone.

An analysis of exemplary CMP was performed on a cohort of four horses. CMP was assayed to determine various proteins present in CMP. Though not exhaustive, FIGs. 7A, 7B, 7C, 7D, and 7E illustrates the protein found collectively in the CMP from four different horses as further described in, for example, Loux SC (2017) Reproduction 153: 197-210, which is incorporated by reference herein for all purposes.

Figure 6:
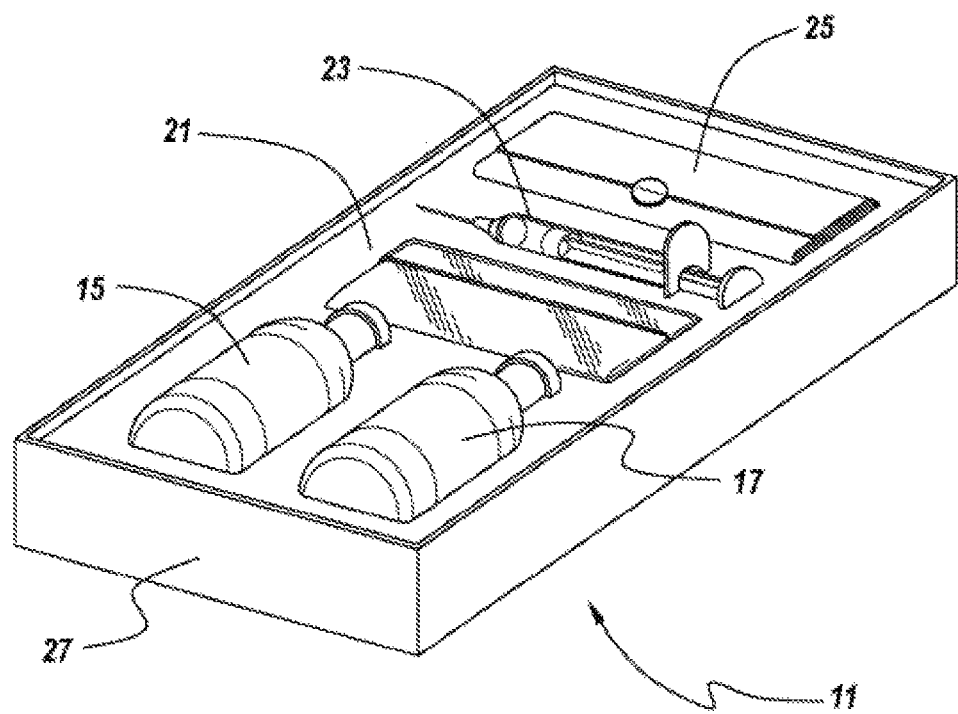
FIG. 6 illustrates a kit, in accordance with various embodiments.

Turning now to FIG. 6, a kit embodying features of the present invention, generally designated by the numeral 11 is depicted. Kit 11 has the following major elements: a first vial 15, a second vial 17, a container for a tissue wrap 21, a syringe 23, and instructions 25. The kit 11 is held in suitable packaging, as depicted, a box 27. Suitable packaging may comprise any means for holding the collection of parts, materials and compositions. For example, without limitation, bags, wraps, containers, ties and the like. First vial may hold a pharmaceutically acceptable carrier. Second vial may hold a medicament comprising a dried particulate mixture of amniotic material and a powdered, lyophilized mixture of cervical mucus plug.

To prepare for use of kit 11, all or a portion of the contents of second vial 17 may be reconstituted with all or a portion of the contents of first vial 15. The reconstituted medicament may be drawn into syringe 23 and administered subcutaneously to a subject.

Advantageous and novel concepts for various embodiments of the regenerative and antimicrobial biological medicament described herein is that it is "off the shelf" and does not involve invasive collection from the animal needing treatment, adulteration, further processing, or culture, but is a completely natural product that can be given on the day of diagnosis. It has an extremely high safety profile with infrequent and mild side effects (i.e. transient and self-limiting injection site swelling) and it is not tumorigenic.

Protocols for administration of medicaments in accordance with various embodiments are found herein below in the Examples. In addition, prophylactic administration is also contemplated. For example, in a quarantined barn or pen where one animal subject is infected with an infectious disease, animals exposed to the infected animal may be subject to one dose of the medicament (e.g., administered subcutaneously) on the first day of the identification of the infected animal subject and then a subsequent dose on the fourth day after the identification of the infected animal subject. In light of an established infection, an intravenous, intratracheal, intraperitoneal, intraabdeominally or intralesionally during surgery, perilesionally, or intrathecal injection or route of administration may be warranted and at more frequent intervals or additional doses as clinical condition and response indicates. In further embodiments this may be considered to be given in conjunction with antimicrobials, and other compounds. Separate individualized protocols may exist for each instance and goal. In further embodiments, an implant loaded with medicament may be implanted into an animal subject to effect long-acting administration. Such an implant may be comprised of a synthetic material or may be comprised of fetal tissue. In various embodiments, medicaments in accordance with various embodiments are chemically joined to a polymeric implant for implantation into the body of an animal, controlling the rate of release of the medicament.

In various embodiments, administration of medicaments in accordance with various embodiments may be performed on a prophylactic basis with annual administration. Further, administration may depend on exposure of the subject animal (e.g., a horse), which is related upon number of shows, traveling, boarding circumstances, etc. In that regard, the greater number or duration of exposures may indicate the need for administration after such exposure or on a more frequent (e.g., biannual or even quarterly or monthly) basis. This administration would also be expected to help with indications for which the subject animal is already undergoing treatment, for example use of amnion for tendon/ligament injury, reproduction, osteoarthritis, bone & hoof issues, ocular, wounds, dental treatments, autoimmune, and other inflammatory-based conditions, in addition to the immune prophylactic protection against diseases. In that regard, administration of medicaments in accordance with various embodiments may be used as an adjunct to conventional medical treatments. As described herein, the suspension agent (PEG) appears to provide a more uniform suspension and enables more accurate dosing ability.

Moreover, medicaments in accordance with various embodiments may be used to treat a variety of diseases, whether infectious or otherwise, in various animals, and efficaciously even when administered at different stages of disease and to patients with differing levels of severity. For example, it is contemplated that medicaments in accordance with various embodiments may be used in management of exuberant/aberrant inflammation in inflammatory bowel disease in dogs and cats, stomatitis in cats; pancreatitis and hepatitis in dogs, proud flesh in horses, exercise-induced pulmonary hemorrhage and asthma in horses, asthma in cats, autoimmune skin disease in dogs atopic dermatitis and autoimmune-based keratoconjunctivitis sicca, hypothyroidism, and diabetes in dogs and cats. Furthermore, medicaments in accordance with various embodiments may be useful in the treatment of tumors—both external and internal in dogs and cats, and sarcoids/squamous cell carcinomas/melanomas in horses.

Medicaments in accordance with various embodiments may be useful in treatment of infectious agents and exuberant/aberrant inflammation disorders, including equine herpes virus myeloencephalitis, equine influenza virus, equine infectious anemia, West Nile Virus, equine encephalides, piroplasmosis, and strangles in horses, kennel cough and parvovirus in dogs, feline infectious peritonitis in cats, feline immunodeficiency virus, feline leukemia virus, feline distemper virus, rabies, Lyme and other tick-borne disease in dogs, distemper virus in dogs, *pseudomonas* in canine ear infections, Methicillin-resistant *Staphylococcus aureus* ("MRSA") in dogs/horses, pythiosis in horses, guttural pouch mycoses in horses, Equine protozoal myelitis in horses, leptospirosis and Equine Recurrent Uveitis, other equine respiratory pathogens, equine diarrhea-causing pathogens (bacteria, virus, protozoa), leptospirosis, tick-borne diseases (i.e. Lyme Disease, Anaplasmosis), equine protozoal myeloencophalitis, and other infectious diseases. Medicaments in accordance with various embodiments may be useful in treatment of diseases in canids such as, but are not limited to, canine respiratory pathogens (*Bordatella bronchiseptica*, parainfluenza virus, distemper virus, adenovirus type 2, and canine herpesvirus), diarrhea causing viruses or bacteria (i.e. parvovirus, coronavirus, rotavirus, canine adenovirus *Clostridium perfringens/difficile, Campylobacter jejuni, Escherichia coli, Salmonella* spp, coccidia, *Isospora* spp, Giardia, *Cryptosporidium* spp, etc.), leptospirosis, tick-borne diseases (i.e. anaplasmosis, Lyme Disease, ehrlichiosis, Rocky Mountain Spotted Fever), and other infectious diseases. Medicaments in accordance with various embodiments may be useful in treatment of diseases in felids including, but not limited to, Feline Infectious Peritonitis (FIP), Feline Immunodeficiency Virus (FIV), Feline Panleukopenia (FP), Feline Leukemia Virus (FeLV), Feline Viral Rhinotracheitis (FVR), *Chlamydophila*, Feline Calcivirus (FCV), Ringworm, Feline *Bartonella, Giardia*, Coccidia, and Tularemia.

Medicaments in accordance with various embodiments, as discussed herein, may be used in products intended to treat joints, bones and hooves, tendon/liagments, ocular diseases, organ-related diseases, wounds, medication resistant infections, surgical applications, and dental applications.

Medicaments in accordance with various embodiments, as discussed herein, may be delivered in a variety of formulations depending upon route of administration, medical indication, and other medically relevant factors. For example, medicaments in accordance with various embodiments may be formulated in a manner to vaporized with a nebulizer and/or formulated as an intranasal spray. Moreover, medicaments in accordance with various embodiments may be formulated as hydrogels, embedded on wraps, and/or micronized. Further embodiments include formulation as nanoparticles, extended-release implants, transdermal and transmucosal controlled release delivery systems, m16 nasal and buccal aerosol sprays, drug-impregnated lozenges, encapsulated cells, oral soft gels, microneedle patches, ultrasound guided delivery, iontophoretic devices to administer drugs through skin, encapsulation formats, including micelles and liposomes, and a variety of programmable, implanted drug-delivery devices. Technology has been formulated in doses that allow for periarticular or perilesional subcutaneous administration, but can be given intralesionally or intraarticular if necessary.

Example 1: Collection & Preparation of Decellularized Amniotic Material

Chain of custody of birth tissues used in amnion and/or amnion+CMP embodiments is retained. Donor mares are admitted approximately 30 days prior to foaling for acclimation after extensive health and history questionnaire, thorough physical examination, consent to foal at ranch by owner, extensive infectious disease screening.

Extensive Infectious Disease Testing:
 Test Kit #1 Mare Screening Prior to Admittance to Ranch for Foaling
  Equine Respiratory REALPCR Panel (Comprehensive; deep nasal swab & whole blood samples)
   Equine adenovirus, equine influenza virus (EIV/H3N8), equine herpesvirus type 1 (EHV-1), type 2 (EHV-2), type 4 (EHV-4) and type 5 (EHV-5), equine rhinitis A virus
   (ERAV), equine rhinitis B virus (ERBV), *Streptococcus dysgalactiae* subsp *equisimilis, Streptococcus equi* subsp. *equi*, and *Streptococcus equi* subsp. *zooepidemicus* RealPCR™ tests. Includes culture (organism ID only) on selective media for beta-hemolytic *Streptococcus* Spp.
  *Leptospira* spp. RealPCR™ Test (whole blood & urine samples)
   Pathogenic strains only
  McMaster Fecal Egg Count (fecal sample)
  Dourine (*Trypanosoma equiperdum*)—NVSL (serum sample)
  Glanders (*Burkholderia mallei*)—NVSL (serum sample)
  Brucellosis (*Brucella abortus*)—NVSL (serum sample)
  Piroplasmosis (*Babesia caballi*) cELISA—NVSL (serum sample)
  Piroplasmosis (*Babesia caballi*) CF—NVSL (serum sample)
  Piroplasmosis (*Babesia* (*Theileria*) *equi*) cELISA—NVSL (serum sample)
  Piroplasmosis (*Babesia* (*Theileria*) *equi*) CF—NVSL (serum sample)
  Equine Viral Arteritis (EVA)—NVSL (serum sample)
  Equine Hepatitis Virus PCR Panel—Cornell (serum sample)
   Equine Parvovirus and Equine Hepacivirus (EqHV) (Non-Primate Hepacivirus—HPHV) PCR.
  Neonatal Isoerythrolysis—UC Davis (serum sample)
  *Anaplasma* spp. RealPCR™ Test (serum sample)
   *Anaplasma Phagocytophilum* and *Anaplasma* platys RealPCR™ test.
  Equine Infectious Anemia (EIA; serum sample AGID test)
  Contagious Equine Metritis—UC Davis (Clitoral Fossa and Clitoral Sinus Swabs)

Test Kit #2 (Further Mare Testing Upon Arrival to Farm)
  Custom Large Animal Profile (serum and whole blood samples)
   Panel includes: ALB, A:G ratio, ALP, Anion gap, AST, DBIL, IBIL, TBIL, BUN, B/C Ratio, Ca, Cl, CHOL, CK, CREA, GGT, GLOB, GLU, PHOS, K, TP, Na, Na:K Ratio,
   TCO2, SDMA, RBC, WBC, HCT, HGB, Erythrocyte indices, WBC differential, platelet
   estimate, Fibrinogen by heat precipitation.
  Urinalysis, Complete (urine sample)
   Volume, color, clarity, specific gravity, pH, protein, glucose, ketones, urobilinogen,
   bilirubin, blood, WBC, RBC, bacteria, EPI cell, mucus, casts, crystals.
  Equine Diarrhea RealPCR™ Panel (fecal sample)
   *Clostridium difficile* toxin A gene, *Clostridium difficile* toxin B gene, *Clostridium Perfringens* alpha toxin (CPA) gene, *Clostridium perfringens* CPnetE/F toxin gene, *Cryptosporidium* spp., equine coronavirus, equine rotavirus, *Lawsonia intracellularis, Neorickettsia risticii* (Potomac Horse Fever), *Rhodococcus equi*, and *Salmonella* spp. RealPCR™ tests. If the RealPCR test is positive for *Salmonella* spp., a culture with susceptibilities on selective media for *Salmonella*.
  Lyme Disease, Equine Multiplex—Cornell (serum sample)

Test Kit #3 (Immediately Post-Foaling; Amnionic Fluid Sample)
  Equine Hepatitis Virus PCR Panel 2—Cornell
   Equine Parvovirus and Equine Hepacivirus (EqHV) (Non-Primate Hepacivirus—HPHV) PCR.
  *Leptospira* spp. RealPCR™ Test
  *Salmonella* spp. RealPCR™ Test with Culture, ID only
  *Neospora caninum* spp./and *Neospora Hughesi* RealPCR™
  West Nile Virus RealPCR™ Test
  *Anaplasma* spp. RealPCR™ Test
   *Anaplasma Phagocytophilum* and *Anaplasma* platys RealPCR™ test.
  *Borrelia burgdorferi* spp. by RealPCR™ Test
  Equine Herpesvirus Types 1 (EHV-1) and 4 (EHV-4) RealPCR™ Tests
  *Toxoplasma gondii* by RealPCR™ Test
  EPM *Sarcocystis neurona* PCR—Equine Diagnostic Solutions Test Kit #4 (Final Product Testing)
  Ea. Cell Line Sterility Profile 1 and Anaerobic Culture
   Direct inoculation on a battery of eight media, incubated for a period of 10 days.
  Ea. STAT-*Mycoplasma* spp. PCR Testing—Biological Material Testing
   Sample type: 1 vial of 1 mL of amnion fluid Beginning 7-14 days prior to expected foaling date, milk is tested once daily for pH, Ca++ levels, and color change and twice daily when a week out from expected parturition. When test indicates birth is nearing, barn watch begins for behavioral signs of eminent parturition until foaling and collection occurs.

Birth tissue collection is via natural foaling and not scheduled C-section

This is not an aseptic process but should be carried out as aseptically as possible.

Care should be taken when working with animals due to unpredictable behavior.

To ensure concurrent documentation, it is recommended that an individual not involved in the collection fill out form PR11.F1 Tissue Collection Record.

If possible, tail should be wrapped before parturition.

Applicable PPEs should be worn throughout the process.

Fluid Collection

Once the water breaks on the donor horse, rush to the horse with a chuck pad and place the chuck under the rear of the donor horse. The individual collecting the fluid should be gowned up with gloves on. Prepare the suction apparatus by connecting the bucket to the suction device and power on the device. Wait for the amniotic sack containing the foal to present. The foal should come out with the front hooves facing outward followed by the head.

Using scalpel, pierce the amniotic sack on the superior surface. This will allow access to the fluid without allowing it to drain out. Insert the suction tip into the hole created and begin fluid collection. Continue collecting fluid until the sack is empty. Once the fluid has been collected, power off the suction device and begin aiding the horse in delivering the foal.

Membrane Collection

Once fluid collection is complete, begin to help deliver the foal. Begin pulling out the foal while carefully removing the membrane as you go. Attempt to keep the sack on top of the chuck placed in the beginning. You can use scissors to cut away the sack if necessary. Once removed, cut the umbilical cord using a scalpel and place the membrane in a collection bucket. Placenta is tied off and not collected and is normally expelled within 3 hours of birth. Chorionic membrane in horse is separated from amnionic sac that is presented at birth. If other material is to be collected such as the mucus plug, umbilical cord, or placenta, collect the items at this time and wash according to the "membrane wash" section. Placenta is tied off and not collected. Chorionic membrane in horse is separated from amnionic sac that is presented at birth.

Membrane Wash

Keep the membrane in the bucket as you prepare the sink area for cleaning. Clean the entire area with bleach and follow with isopropanol wash before opening the bucket. Open the bucket and begin to rinse the membrane using the sprayer to remove any debris that may have accumulated during the collection process. With the membrane outside the bucket, use bleach and isopropanol to clean the bucket. Replace the membrane in the bucket with saline and continue to wash. Repeat this three times or until the entire membrane has been inspected and cleaned as best as possible. Once wash is completed, add 250 ml of saline to the collection container with the membrane inside. Add 6.25 ml of 2% chlorhexidine to the collection bucket. If more saline is used, you can add more chlorhexidine at a ratio of 25 ml/liter. At this stage ensure all containers with tissue are labeled with the donor number and tissue type.

Amnionic Fluid Processing (novel in fact of counting viable cells and placing specific number of donor SCs (epithelial SC and MSC) uncultured back into cryopreserved product at different strength levels.

CMP Processing. Processed by being washed with water until clean after collection at foaling, placed into plastic bag. Cut into smaller pieces upon arrival to lab and immediately frozen to −80 degrees. Lyophilized and freeze-dried to dehydrate, cryomilled, not filtered, mixed usually 3:1 with amnionic membrane powders, sterilized.

Membrane Powder Filtration. Done in dry form with vortexer; filter used to accomplish desired particle size if necessary for application vs time of cryofracture). These different powder groups are then used for reconstituted, off the shelf products and used in the cryopreserved product.

Large, particulized amnion component of embodiment with CMP. Comprised of >70 micron cryofractured amniotic membrane powder (also known as retentate). This product is novel in that it cannot be injected intravenously due to large particle size, which also contributes to its effectiveness in non-healing or difficult wounds and bone issues, because it stays in the area injected for a sustained time-release effect because it is too large in particle size to be removed by circulation and/or lymphatics.

Another novel concept is dosing is important in all considerations of effect, including amount of specific particulate powder, size of particles, amnionic fluid, and stem cells (both epithelial and mesenchymal from donor), depending on application.

CMP may be processed in a similar manner as described above, undergoing dehydration ad cryofactionation. For example, CMP may be collected at foaling and washed with water until clean and placed into plastic bag. The washed CMP may be cut into smaller pieces and frozen to −80 C degrees. The CMP may later be lyophilized/freeze-dried to dehydrate the CMP. The dehydrated CMP may then be cryomilled, without filtration filtered.

Example 2

Medicaments in various embodiments disclosed herein may be useful in the treatment of equine colic. The equine is uniquely susceptible to painful abdominal complications colloquially known as "colic." The term "colic" is generic and nonspecific; it does not specify or indicate etiology of the horse's pathology. Of the organs within the abdomen, the gastrointestinal tract is the main origin of colic symptoms. These gastrointestinal pathologies can often be managed medically, however, a significant percentage are referred for surgical intervention. While the exact incidence of colic in horses is not well established as location, management, age, etc. vary greatly and affect presentation and outcome. Literature often recites the incidence as between 3.5-26 colics/ 100 horses per year. Of those horses, it has been further reported that approximately 2% undergo surgical intervention.

Operating a surgical colic has many considerations and challenges. Of note and interest here, is the complication of surgical site infections (SSIs) post ventral midline exploratory celiotomy. It has previously been documented that between 7.4-43 percent of ventral midline exploratory celiotomies in the horse are followed by an SSI. The high rate of this complication is of concern as it can diminish the integrity of the incision and ultimately the body wall and in some situations, result in humane euthanasia of the horse. It is for these reasons that veterinarians have long tried varied interventions to address SSIs. To-date, many practices are in use, but none stand significantly above the others in success.

A prospective study is to be conducted using medicaments in accordance with various embodiments, for example, an allograft comprising acellular amnion scaffolding atop the linea alba and underneath the skin and subcutaneous tissue of randomly selected horses that undergo colic surgery. These horses will be compared against a control group to assess degree of edema, drainage, and cultured organisms associated with the incision.

It is expected to include up to 200 horses in this study; 100 within the treatment group and 100 control. Very preliminary data as the study has just gotten underway in stands at N=6 horses have not gotten SSIs, which could be predicted based on the innate antimicrobial activity of amnion. If implantations continue to prevent SSIs, it would be expected that injections along the incision with birth tissue composites containing CMP in addition to amnionic membrane will be enhanced over the effects of amnionic membrane alone.

Example 3

Extracellular vesicles (EVs) are small, membrane-bound particles secreted from all cell types that have an important role in cell signaling and cell-to-cell communication. They form by budding from the cell membrane or from multivesicular bodies or and move through the circulatory system to release their contents into another cell. It has been discovered that the primary mechanism of action of stem cells is via paracrine actions rather than their ability to differentiate. EVs can transfer signaling molecules including lipids, mRNAs, proteins, and non-coding RNAs including miRNAs to another cell. More specific effects of EVs includes maintaining homeostasis of the body in terms of repair and inflammatory status, regulation and modulation of the immune system to provide anti-inflammatory healing environment, angiogenesis, decreased apoptosis of injured tissue-specific cells, secretion of growth factors and cytokines, activation of signaling cascades important for healing, and recruitment of endogenous stem cells and proliferation. Currently, EVs and their signaling are thought to aid in and positively impact a variety of medical problems including non-healing wounds, heart attacks, acute kidney failure, neurological disorders and injuries, cancer, lung diseases, autoimmune disorders. It is believed that EVs are present in the amnionic fluid (AF) as well as dehydrated amnionic tissue and are the primary influencer of effects. After testing a filtration method and a PEG concentration method for equine AF-EVs, cell growth was observed to increase, thus supporting the presence of EVs in AF.

Methodology 50 ml of AF-EVs were collected from equine amniotic fluid collected during the birthing process. The material was were filtered through a 0.45 and 0.22 micrometer filter to sterilize the solution and then had the cells extracted from it. The material was stored at −80° C. after that for a year.

Two different techniques were used to concentrate the AF-EVs. The first concentration method is by ultrafiltration. The principle behind this technique is to remove larger particles first and then smaller particles by separating it from the filtrate at the next stage. Thus, the AF-EVs of a specified size range are concentrated. AF-EVs sized in the 220 to 100 micrometer diameter range, in particular, were collected by this procedure.

The AF was previously filtered through a 0.22 micrometer filter which separated the larger particles so the only step would be to separate all the liquid and smaller particles from it. The thawed AF was filtered through a 0.1 micrometer polyethersulfone membrane bottle-top vacuum filter system with a filter capacity of 500 mL. The top of the 0.1 micrometer membrane was washed 20 times with 600 microliters of phosphate-buffered saline (PBS). PBS is a buffer solution that maintains a constant PH that is similar to the human body so therefore it will not affect the cells when the treatment is applied. This method will have concentrated all particles within the 220 to 100 micrometer diameter including the AF-EVs within the AF.

The second concentration method was done by precipitation which is the second most used isolation method for EVs. The principle behind this method is to reduce the solubility or the ability to be dissolved in a liquid of certain particles. The 6000 polyethylene glycol (PEG) used is not toxic to the cells so will not affect cell growth when the treatment is applied. Initially, a 50 ml stock solution was created that had a 16% PEG concentration and a concentration of 1-molar sodium chloride. Next, the stock solution was added to the thawed amniotic fluid, mixed by inversion, and then refrigerated overnight. The next day the solution was spun with a tabletop centrifuge at about 3 thousand times gravity. After centrifugation, the top liquid was poured off and the pellet at the bottom was resuspended in 600 microliters of PBS.

Because the PEG is not sterilized when added to the solution, the PEG treatment must be sterilized before it can be added to the cells. This was also applied to the filtration treatment to reduce the potential interface the sterilization procedure has on the results. A 3 ml syringe with a filter with 0.2 micrometer pore size was repurposed to sterilize the treatments. The needle was taken off and the liquid was poured into the syringe to be pushed through the filter to sterilize the liquid.

The next step in the procedure is to measure the treatment's effect on cell growth. The two concentration techniques were tested against PBS and AF as a control. PBS was used as a control to demonstrate normal cell growth without interference and AF was used as a control to demonstrate that the results were due to the concentration method and not various components in the amniotic fluid. 1.13 million cells were counted using a hemocytometer and then plated in a T-25 cell flask so that the cells were plated at 15% confluence. 0.250 microliter of each treatment was applied to two cell plates and the cell count was measured by a hemocytometer after about 24 hours. To measure with a hemocytometer, first the cells were detached from the bottom of the plate by 25% Trypsin EDTA. Then they were collected with 2 ml of medium into another tube. 40 microliters of Trypan blue solution and the solution with the media and cells were mixed. Next, 10 microliters of that solution were put onto the hemocytometer and 5 boxes of cells were counted using a microscope. The total cell count in those 5 boxes was used to find the total cell count per plate after 18 and 42 hours of growth.

Results

|  | Treatment type | | | |
| --- | --- | --- | --- | --- |
| Treatment times (hours) | PBS (million cells) | AF (million cells) | Filtration (million cells) | PEG (million cells) |
| 0 | 1.13 | 1.13 | 1.13 | 1.13 |
| 18 | 3.32 | 3.53 | 3.32 | 4.25 |
| 42 | 6.55 | 8.12 | 7.86 | 8.08 |

The PBS as expected had the slowest growth because nothing was added that would have affected the cells. The PBS and filtration concentration methods proved to have equally slow initial growth. While the filtration method had a higher growth rate after the second measurement it still was much slower than AF. This means that the filtration method demonstrated no significant effect on cells. One of the reasons it had no effect could be because the EVs got damaged by pressure due to the vacuum on the other side of the filter or the EVs did not stay on the surface of the filter membrane or stuck to it so they could not be removed from the top.

The PEG treatment had a higher initial cell count and a similar cell count the second time compared to the AF treatment. Cells grow logarithmically which means that they slow down and stop growing at a certain point. For these cell plates, growth stops at about 8 million cells. So, both the PEG and AF treatment likely stopped doubling some time before the second measurement. Therefore, the first cell count should be relied on to compare growth rates for those two treatments. The initial doubling time can be used to compare growth rates. The treatments had an initial doubling time as followed: PBS-11.58 hours, Filtration-11.58 hour, AF-10.95 hours, PEG-9.48 hours. PEG had the lowest doubling time out of the four treatments. It was 2 hours faster than both the filtration isolation method and the PBS and it was an hour and a half faster than the amniotic fluid treatment. Because it has a lower doubling time, then PBS there are properties of the treatment that can increase the proliferation rate. More importantly, the fact that concentrating the EVs leads to a lower doubling time compared to amniotic fluid demonstrates that there is a potential healing benefit from concentrating AF-EVs.

The AF-EVs were highly concentrated based on the PEG procedure used. This demonstrates that concentrating the AF-EVs by the PEG method did lead to a greater growth rate and therefore demonstrating that AF-EVs does have an effect on cell growth. This equates to a healing benefit of EVs because concentrating AF-EVs also increases proliferation rates of the cells.

EVs have one of the most important roles in cell-to-cell communication because they have the ability to cause a wide range of effects by targeting specific cell types and delivering molecules that can change a cell's actions. The effects of different EVs depend on the parent's cell function.

Example 4

An outbreak of equine herpes virus myeloencephalitis (EHM) was identified in a facility with equines. A quarantine of 700 horses, including 112 in the affected barn, was imposed. Age range of the horses were 2-22 years. There were 37 mares, 4 stallions, and 71 geldings. For 10 days, biosecurity measures in addition to allografts including dried particulate mixture of amniotic material were administered to the 112 horses in the affected barn. Allografts including dried particulate mixture of amniotic material were administered 3-8 days apart.

Horses were monitored by quantitative nasal swab and whole blood PCR testing, serum amyloid A testing, complete blood counts (cbc's), serum chemistry panels (cp's), virus isolation (final day), RNA testing to confirm active and/or latent infections and physical/neurologic examinations. No new cases were detected after baseline administration, thus indicating reduced number of horses with active infections. 21/112 horses were positive at baseline with 4/112 incubating at baseline that later become positive. A rapid reduction of viral loads as measured by nasal shedding was observed, and most infections were cleared inside of 3 days after amnion implantation. All positive horses were no longer shedding or at non-infective levels within 10 days based on DNA/RNA quantitative PCR and virus isolation. A "super shedder" horse (peak 70 million/106 cells) become non-infective in 10 days. In addition, there was a decreased incidence, duration, and level of viremia and subsequent neurologic disease, rapid resolution of neurologic cases, 0% mortality after amnion implantation, shortened outbreak and quarantine time, and safe with only minor self-limiting injection site reactions in a few horses and no aberrations in cbc's or cp's.

It is theorized that the effects are primarily paracrine in nature. EHM lesion similar to ischemic stroke lesion in humans was treated successfully. Moreover it is believed that upregulation of necessary innate/adaptive inflammatory response (certain level of inflammatory response necessary for healing) is induced by treatment. Further, immunomodulation—selective suppression and/or resolution of exuberant inflammatory response is believed to occur (i.e. WBC infiltration, lymphocyte proliferation, cytokine storm, vasculitis, necrosis, myeloencephalitis, microthrombi via M1 to M2 macrophage polarization and increased Treg cells). An anti-inflammatory response (i.e. IL-10, IL1RA, M1-M2 macrophage shift) was also observed, as well as a neuroprotective response.

The above study was done with multiple combinations of amnion derived allografts, mostly large particle (>70 µm) dehydrated amnionic membrane, but also smaller particle (<70 µm) dehydrated amnionic membrane alone, and combined with stem cells and amnionic fluid. Anecdotal reports and preliminary research in cattle suggest that addition of CMP further enhances efficacy with regards to prophylactic infectious disease protection, and since the immune system is operating optimally, enhanced growth, quality of tissue, and feed efficiency. Anecdotal reports of field treatments with the addition of CMP to the equine dehydrated amnion immune support product are favorable as well for multiple infectious diseases, including viral and bacterial respiratory and diarrhea diseases, as well as infection-related dermatological and protozoal diseases such as equine protozoal myeloencephalitis. 3 outbreaks of EHM have responded extremely favorably in eliminating EHV-1 infection and stopping the spread, bringing resolution and rapid return to health during field outbreaks. All of this is more fully substantiated by the raccoon parvo data trials, first with dehydrated large particle amnion and then second with more significant elimination of infection and healing of damaged intestinal tissue when the CMP component was added to the dehydrated amnion allograft.

Example 5

A safety study involving a description of the effects over 21 days of an intra-uterine injection of amnion-dehydrated allograft in mares during the breeding season was conducted.

Safety Study Design

Study design involved 12 horses (9 light-breed and 3 Warmbloods) that underwent transrectal palpation, endoscopy, uterine culture (aerobic), cytology, and biopsy (Kenney Doig, staining for fibrosis), as well as blood work, followed by hysteroscopic injection of product (9 product injections and 3 saline injections) on Day 0. Rectal temperatures were monitored daily throughout the study duration. Horses were transrectally palpated and additional blood was drawn on Day 4 for SAA, Fibrinogen, CBC, and Progesterone. On Day 21, the horses were transrectally palpated, re-scoped, and uterine culture, cytology, and biopsy were repeated. Statistics included continuous analysis of data to determine the main effects of group, day, and their interactions using the SAS MIXED procedure with repeated measures. Categorical data was analyzed using the SAS LOGISTIC procedure.

Safety Study Results

No mares experienced an elevation in rectal temperature in the 21 days after injection. No elevation in markers of inflammation, including SAA, Fibrinogen, or WBC) from Day 0 to Day 4 in either the control or treated group. There were no differences in uterine cytology and culture results between groups or between days within groups. Hysteroscopy following injection demonstrated no gross evidence of detrimental effects in any mares examined. There was a tendency ($x^2=0.07$) in an increased frequency of histologic uterine inflammation in control mares compared to treated mares at Day 21. No significant differences were found between groups or interaction of group by day for the pattern of inflammation, presence of periglandular fibrosis, pattern of periglandular fibrosis, number of cell layer surrounding fibrotic glands, number of fibrotic nests, the presence of edema or lymphatic dilation on endometrial histology. Based on data from the safety study, the product was considered safe for intrauterine implantation and could possibly modulate abnormal inflammatory reactions to semen within the uterus post-breeding and have an anti-inflammatory effect, especially in mares with persistent post mating induced endometritis.

Efficacy Study Design

In a 2-part multicenter clinical study, it was hypothesized that post-breeding intrauterine (IU) infusion with a dehydrated amnion-derived allograft (DAA) would enhance pregnancy rates in a clinical setting. A controlled prospective efficacy study of post-breeding IU DAA was compared to ABX in first-cycle barren Thoroughbred mares. Sixty mares that had either failed to get pregnant on two or more cycles in the previous year or which lost a pregnancy were randomly assigned to either an DAA or ABX treatment group at the onset of the breeding season. Mares with no bacterial growth and <5 mm fluid prior to breeding were included in the study and administered IU either DAA diluted in 60 ml LRS or 7.2 Million IU procaine penicillin+ 600 mg gentamicin extended to 60 mL with LRS within 24 hours post-breeding. Mares with intra-uterine fluid were lavaged or received oxytocin as indicated based on clinical presentation. There was no difference in first cycle pregnancy rates of DAA compared to ABX (65% vs 64%, respectively). Based on these results, DAA was used as a component of the reproductive treatment protocols. Retrospective analysis of over 500 breeding cycles from 300 mares was performed to compare pregnancy rate in cycles with no treatment, DAA, DAA/lavage, ABX and ABX/lavage based on the clinical judgement of the attending veterinarian. Pregnancy rates were not different between any group, however, pregnancy rates were numerically highest in cycles treated with DAA/lavage (73% vs 65%).

Safety testing of intrauterine infusion of amnion-derived product as a 60 ml volume 24 hours after breeding alone or in combination with lavage+/−antibiotics does not have a detrimental effect on fertility. Amnion-derived allografts can be safely used with acceptable pregnancy rates and no adverse effect on embryonic loss. This reveals potential for replacement of antibiotics and other treatments for inflammatory (innate reaction to semen and fluid accumulation) and possibly infectious endometritis (persistent post-breeding endometritis in particular), as the mares in the efficacy study may or may not have had negative cultures prior to breeding. This hypothesis is based on the antimicrobial effects that have been repeatedly demonstrated by amnion based technology with regards to non-healing wounds, resistant infections, and infectious disease prophylaxis and therapy. The above efficacy data confirmed that the use of IU DAA is safe and may provide similar benefits to pregnancy rates as other common treatments. The use of post-breeding DAA combined with lavage may be most beneficial. These data are based upon amnion-derived allograft alone infused into the uterus. A new study is currently underway looking at subcutaneous injection of a dehydrated birth tissue composite containing both amnion and cervical mucus plug, which based on other conditions and species to provide enhanced effect and allow subcutaneous injection versus intrauterine infusion.

The detailed description of various embodiments herein makes reference to the accompanying drawings, which show various embodiments by way of illustration. While these various embodiments are described in sufficient detail to enable those skilled in the art to practice the disclosure, it should be understood that other embodiments may be realized and that changes may be made without departing from the scope of the disclosure. Thus, the detailed description herein is presented for purposes of illustration only and not of limitation. Furthermore, any reference to singular includes plural embodiments, and any reference to more than one component or step may include a singular embodiment or step. Also, any reference to attached, fixed, connected, or the like may include permanent, removable, temporary, partial, full or any other possible attachment option. Additionally, any reference to without contact (or similar phrases) may also include reduced contact or minimal contact. It should also be understood that unless specifically stated otherwise, references to "a," "an" or "the" may include one or more than one and that reference to an item in the singular may also include the item in the plural. Further, all ranges may include upper and lower values and all ranges and ratio limits disclosed herein may be combined.

Example 6

A preliminary pilot study was conducted on five cases of Raccoon Parvovirus (RPV) infection where medicaments in accordance with various embodiments, in particular, embodiment comprised of dehydrated amnionic membrane powder, was injected into subcutaneously (hereafter abbreviated as "SC") into racoons. The treatment was in response to a natural RPV outbreak amongst a captive raccoon population. Raccoons develop Parvo in a manner analogous to that seen in canines, ostensibly due to genetic similarities between RPV and the predominant Canine Parvovirus (CPV-2) strain (the CPV-2b subtype) that infects dogs. The treated racoons recovered from the SC injection with no noted adverse effects. Three of the treated raccoons recovered and their liver enzymes restabilized more quickly than the age-related similarly sick (parvo) non treated raccoons. Parvo is highly infectious in raccoon populations and there is a time of susceptibility in young raccoons.

At a later time, 6 baby, bottle feeding raccoons developed diarrhea and fevers. Strict hygiene controls were begun and the 6 raccoons were treated with antibiotics and medicaments in accordance with various embodiments, in particular, embodiments comprising a dried particulate mixture of amniotic material and a powdered, lyophilized mixture of cervical mucus plug. The composition of dried particulate mixture of amniotic material and a powdered, lyophilized mixture of cervical mucus plug was reconstituted with saline and administered to the baby raccoons (800-1000 gram raccoons). Swab samples were collected to confirm parvovirus as the causative agent. One of the babies came back parvo positive by PCR fecal swab. Fevers in the baby raccoons were abated within 2 days and the baby raccoons were subsequently re-dosed at Day 4 with the inventive composition. By the end of seven days these six raccoons had made a recovery and were drinking bottle milk at the same rate as similar size baby raccoons. The weight gain on these raccoons was better and compensatory gain to catch up the weight that they had lost while they were sick. It was expected to have more parvo infected baby raccoons in the nursery facility as there were another 10 small bottle feeding baby raccoons in the nursery facility, but no further spread of parvo virus was observed.

Having no further spread of parvo would be abnormal. Typically, with one or two parvo cases, there is rapid spread through the whole nursery facility and an attack rate of over 98% infections is usually observed. It is not uncommon to have a death rate in over 95% associated with parvo outbreaks. With the inventive composition, in addition to biosecurity and supportive care, death and survival rates have reversed so outbreaks are halted and roughly 95% of infected raccoons survive to be of the age for release into the wild (6-9 months of age) once they are able to collect and eat hard food. This is a significant improvement over the reduction in death rate to 40% from 95% with administration of a dried particulate mixture of amniotic material alone (i.e., without the powdered, lyophilized mixture of cervical mucus plug). The inventive composition, which here contained dehydrated amnionic membrane powder and CMP performed even better than the large particle amnionic powder alone. Not only were the parvovirus outbreaks halted with inventive allograft implantation, but the immune modulatory and regenerative properties of the technology were able to heal the pathogen-induced damage to the intestinal epithelium to stop the clinical manifestation of vomiting/diarrhea and possibly restore the absorptive capabilities of the intestines, allowing the baby raccoons to return to health and catch up to their age-matched, non-infected counterparts, though further studies including resorption would have to be done to confirm this with certainty. Conclusions with regards to the 2 aforementioned groups treated, the first with amnionic membrane powder alone and the second with the combined birth tissue product, were that both were effective but addition of the CMP with additional and inherent antimicrobial properties provided significantly enhanced and more rapid effects in the infectious disease outbreaks.

Example 7

Medicaments in accordance with various embodiments, in particular, embodiments comprising a dried particulate mixture of amniotic material and a powdered, lyophilized mixture of cervical mucus plug which in this Example comprised dehydrated amnionic membrane powder and CMP (the "administered composition") were administered to cattle. A total of 5000 cattle were part of the study, though a portion did not receive treatment with the inventive composition.

No bullers were noted in amnionic membrane+CMP implanted cattle which avoids stress and subsequent economic loss and may be an advantage of not using hormone implants. The deletion of hormonal implants also appeared to be offset by optimization of the immune system and prevention of infectious disease which allows less energy go to immune system and more energy to be partitioned to growth and the laying down of lean muscle tissue.

Visually, it was noted that the treated cattle have a noticeably different body form from the controls. The treated cattle appear "less paunchy" and seem noticeably longer through the loin area. The cattle have a more juvenile appearance, without heavy shoulder and angular heads. It was observed that any cattle that were implanted with composition for pink eye (conjunctivitis) got better very quickly, as well as successful resolution of comorbidities such as "water belly."

Reduced hair loss from lice infections was observed, which is associated with less rubbing. This should equate to positive gain and less repair to infrastructure. Moreover, no footrots were observed in treated cattle. There were fewer arthritis cattle in sick pen than in previous years (with untreated cattle).

Treated cattle appear to be more uniform in pens. By this it is meant that the variations that would normally be present do not appear to be as large. Stated another way, we do not have a steer that is 6" taller than a pen mate and 200 lbs heavier.

It was also observed that treated cattle ate less total mass of feed (estimate around 15% less feed) than untreated cattle without sacrificing increased ADG and greater feed efficiency. Moreover, the treated cattle had very low rates of commonly observed disease or infestation once stabilized. Ring worm was almost nonexistent and if an incident occurred it was short lived and disappeared on its own, without treatment, which is understood to be an indication that the immune system was quickly activated. Observed eye problems were minimal, and those that did occur were treated with a sub palpebral ¼cc injection of administered composition and healed without exception. Three anterior chamber infections (hypopyon) recovered within 10 days of sub palpebral injection. No ectoparasite infection(lice) was noted to have occurred in treated cattle.

Cattle from treated pens retained a noticeably more juvenile body form than untreated steers. Heads necks and shoulders were smoother and smaller and less masculinized. No riding behavior was noted during the winter.

As the study progressed, treated cattle consumed substantially less feed than that of untreated cattle (estimated 25% decrease in daily feed uptake). It is believed that increased feed conversion efficacy to a possibly more powerful and effective immune system are reasons for this decrease. This likely manifests itself in reduced subclinical and chronic disease, for example, parasite load and chronic *Haemophilus*. Lack of subacute and sub-clinical health issues may task the immune system less heavily in the treated pens.

The frame structure of treated cattle were observed to be much less angular and longer on treated cattle than controls. It appears that treated cattle have lighter bone structure and more top line than controls. The control cattle appear to retain rough winter coats longer than treated cattle once daylight length began to increase. Untreated cattle may have a weight advantage at this weighing likely attributed to greater "paunch" volume and denser bone structure, though this difference will likely disappear as the test cattle mature.

Amnion and CMP may delay skeletal maturation and masculinization. This may explain the morphological variations between amnion and CMP treated cattle and untreated animals.

Overall feed consumption of treated animals may be lower than controls. There may be a significant feed efficiency advantage gained by use of amnion and CMP. There were also fewer losses to riding and aggression, and less jostling should equate to fewer injuries during feeding period.

It is highly probable that these results reveal multiple manifestations of immune system modulation as a result of treatment.

Benefits, other advantages, and solutions to problems have been described herein with regard to specific embodiments. It should be noted that many alternative or additional functional relationships or physical connections may be present in a practical system. However, the benefits, advantages, solutions to problems, and any elements that may cause any benefit, advantage, or solution to occur or become more pronounced are not to be construed as critical, required, or essential features or elements of the disclosure. The scope of the disclosure is accordingly to be limited by nothing other than the appended claims, in which reference to an element in the singular is not intended to mean "one and only one" unless explicitly so stated, but rather "one or more." Moreover, where a phrase similar to "at least one of A, B, or C" is used in the claims, it is intended that the phrase be interpreted to mean that A alone may be present in an embodiment, B alone may be present in an embodiment, C alone may be present in an embodiment, or that any combination of the elements A, B and C may be present in a single embodiment; for example, A and B, A and C, B and C, or A and B and C.

Systems, methods and apparatus are provided herein. In the detailed description herein, references to "one embodiment," "an embodiment," "various embodiments," etc., indicate that the embodiment described may include a particular feature, structure, or characteristic, but every embodiment may not necessarily include the particular feature, structure, or characteristic. Moreover, such phrases are not necessarily referring to the same embodiment. Further, when a particular feature, structure, or characteristic is described in connection with an embodiment, it is submitted that it is within the knowledge of one skilled in the art to affect such feature, structure, or characteristic in connection with other embodiments whether or not explicitly described. After reading the description, it will be apparent to one skilled in the relevant art(s) how to implement the disclosure in alternative embodiments.

Numbers, percentages, or other values stated herein are intended to include that value, and also other values that are about or approximately equal to the stated value, as would be appreciated by one of ordinary skill in the art encompassed by various embodiments of the present disclosure. A stated value should therefore be interpreted broadly enough to encompass values that are at least close enough to the stated value to perform a desired function or achieve a desired result. The stated values include at least the variation to be expected in a suitable industrial process, and may include values that are within 10%, within 5%, within 1%, within 0.1%, or within 0.01% of a stated value. Additionally, the terms "substantially," "about" or "approximately" as used herein represent an amount close to the stated amount that still performs a desired function or achieves a desired result. For example, the term "substantially," "about" or "approximately" may refer to an amount that is within 10% of, within 5% of, within 1% of, within 0.1% of, and within 0.01% of a stated amount or value.

Furthermore, no element, component, or method step in the present disclosure is intended to be dedicated to the public regardless of whether the element, component, or method step is explicitly recited in the claims. No claim element herein is to be construed under the provisions of 35 U.S.C. 112(f) unless the element is expressly recited using the phrase "means for." As used herein, the terms "comprises," "comprising," or any other variation thereof, are intended to cover a non-exclusive inclusion, such that a process, method, article, or apparatus that comprises a list of elements does not include only those elements but may include other elements not expressly listed or inherent to such process, method, article, or apparatus.

Finally, it should be understood that any of the above described concepts can be used alone or in combination with any or all of the other above described concepts. Although various embodiments have been disclosed and described, one of ordinary skill in this art would recognize that certain modifications would come within the scope of this disclosure. Accordingly, the description is not intended to be exhaustive or to limit the principles described or illustrated herein to any precise form. Many modifications and variations are possible in light of the above teaching.

What is claimed is:

1. An article of manufacture comprising:
   a dried particulate mixture of amniotic material; and
   a powdered, lyophilized mixture of cervical mucus plug.

2. The article of manufacture of claim 1, wherein the dried particulate mixture of amniotic material comprises particles of a diameter between <500 microns and >70 microns.

3. The article of manufacture of claim 1, wherein the powdered, lyophilized mixture of cervical mucus plug comprises particles of a diameter between <500 microns and >70 microns.

4. The article of manufacture of claim 1, wherein the dried particulate mixture of amniotic material is decellularized by cryofractionation.

5. The article of manufacture of claim 1, wherein the dried particulate mixture of amniotic material comprises at least one of amnion or amniotic fluid, and the amnion is subject to diafiltration by centrifuging the amnion through dialysis membranes with a pore size of 70 microns.

6. The article of manufacture of claim 5, further comprising PEG, wherein the dried particulate mixture of amniotic material and powdered, lyophilized mixture of cervical mucus plug are suspended in the PEG.

7. The article of manufacture of claim 1, further comprising at least one of a sterile, non-pyrogenic isotonic solution or an amniotic fluid.

8. The article of manufacture of claim 1, wherein the powdered, lyophilized mixture of cervical mucus plug is derived from at least one of the same or different species as the dried particulate mixture of amniotic material.

9. The article of manufacture of claim 1, wherein the powdered, lyophilized mixture of cervical mucus plug comprises an interleukin.

10. The article of manufacture of claim 1, wherein the article of manufacture comprises 1% by weight powdered, lyophilized mixture of cervical mucus plug and 99% by weight dried particulate mixture of amniotic material.

11. The article of manufacture of claim 1, wherein the article of manufacture comprises a 1:1 ratio of powdered, lyophilized mixture of cervical mucus plug to dried particulate mixture of amniotic material.

12. The article of manufacture of claim 1, wherein the article of manufacture comprises a 1:2 ratio of powdered, lyophilized mixture of cervical mucus plug to dried particulate mixture of amniotic material.

13. A kit comprising:
    a first vial containing a pharmaceutically acceptable carrier; and
    a second vial containing a dried particulate mixture of amniotic material and a powdered, lyophilized mixture of cervical mucus plug.

14. The kit of claim 13, further comprising a syringe.

15. A method of treating an animal comprising:
    administering an effective amount of the article of manufacture of claim 1 to an animal subject in need thereof.

16. The method of claim 15, further comprising administering a second effective amount of the article of manufacture of claim 1 to the animal subject in need thereof at least twenty-four hours after the administration of the effective amount of the article of manufacture of claim 1.

\* \* \* \* \*